(12) United States Patent
Loosmore et al.

(10) Patent No.: US 6,391,313 B1
(45) Date of Patent: May 21, 2002

(54) **MULTI-COMPONENT VACCINE TO PROTECT AGAINST DISEASE CAUSED BY *HAEMOPHILUS INFLUENZAE* AND *MORAXELLA CATARRHALIS***

(75) Inventors: Sheena M. Loosmore, Aurora; Yan-Ping Yang, Willowdale; Michel H. Klein, Willowdale; Ken Sasaki, Willowdale, all of (CA)

(73) Assignee: Aventis Pasteur Limited, Toronto (CA)

( * ) Notice: Subject to any disclaimer, the term of this patent is extended or adjusted under 35 U.S.C. 154(b) by 0 days.

(21) Appl. No.: 09/353,617

(22) Filed: Jul. 15, 1999

(51) Int. Cl.$^7$ ............................................. A61K 39/116

(52) U.S. Cl. ............................... 424/203.1; 424/256.1; 424/251.1; 424/234.1; 424/193.1; 424/203.1; 424/197.11; 530/350

(58) Field of Search ........................... 424/256.1, 251.1, 424/234.1, 193.1, 203.1, 197.11; 435/69.1; 530/350

(56) References Cited

U.S. PATENT DOCUMENTS

| | | | |
|---|---|---|---|
| 4,496,538 A | 1/1985 | Gordon | |
| 5,506,139 A | 4/1996 | Loosmore et al. | |
| 5,603,938 A | 2/1997 | Barenkamp | |
| 5,646,259 A | 7/1997 | St. Geme, III et al. | |
| 5,808,024 A | 9/1998 | Sasaki et al. | |

FOREIGN PATENT DOCUMENTS

| | | |
|---|---|---|
| WO | 94/00149 | 1/1994 |
| WO | 95/34308 | 12/1995 |
| WO | 96/03506 | 2/1996 |
| WO | 96/34960 | 11/1996 |
| WO | 97/36914 | 10/1997 |

OTHER PUBLICATIONS

Barbour, M.L., R.T. Mayon–White, C. Coles, D.W.M. Crook, and E.R. Moxon. 1995. The impact of conjugate vaccine on carriage of *Haemophilus influenzae* type b. J. Infect. Dis. 171:93–98.
Berkowitz et al. 1987. J. Pediatr. 110:509.
Claesson et al. 1989. J. Pediatr. 114:97.
Black, S.B., H.R. Shinefield, B. Fireman, R. Hiatt, M. Polen, E. Vittinghoff, The Northern California Kaiser Permanent Vaccine Study Center Pediatrics Group. Efficacy in infancy of oligosaccharide conjugate Haemophilus influenzae type b (HbOC) vaccine in a United States population of 61,080 children. 1991. Pediatr. Infect. Dis. J. 10:97–104.
Nitta, D.M., M.A. Jackson, V.F. Burry, and L.C. Olson. 1995. Invasive *Haemophilus influenzae* type f disease. Pediatr. Infect. Dis. J. 14:157–160.
Waggoner–Fountain, L.A., J.O. Hendley, E.J. Cody, V.A. Perriello, and L.G. Donowitz. 1995. The emergence of *Haemophilus influenzae* types e and f as significant pathogens. Clin. Infect. Dis. 21:1322–1324.

Madore, D.V. 1996. Impact of immunization on *Haemophilus influenzae* type b disease. Infectious Agents and Disease 5:8–20.
Bluestone, C.D. 1982. Current concepts in otolaryngology. Otitis media in children: to treat or not to treat? N. Engl. J. Med. 306:1399–1404.
Ioannidis, J.P.A., M. Worthington, J.K. Griffiths, and D.R. Snydman. 1995 Spectrum and significance of bacteremia due to *Moraxella catarrhalis*. Clin. Infect. Dis. 21:390–397.
Meyer, G.A., T.R. Shope, N.J. Waeker, Jr., and F.H. Lanningham. 1995 *Moaxella (Branhamella)catarrhalis* bacteremia in children. Clin. Pediatr. 34:146–150.
Enright, M.C. and M.H. McKenzie. 1997. *Moraxella (Branhamella) catarrhalis*– clinical and molecular aspects of a rediscovered pathogen. J. Med. Microbiol. 46:360–371.
Barenkamp, S.J., and F.F. Bodor. 1990. Development or serum bactericida activity following non–typable *Haemophilus influenzae* acute otitis media. Pediatr. Infect. Dis. 9:333–339.
Barenkamp, S.J., and J.W. St. Geme III. 1994. Genes encoding high–molecular weight adhesion proteins of non–typeable *Haemophilus influenzae* are part of gene clusters. Infect. Immun. 62:3320–3328.
St. Geme III J.W., V.V. Kumar, D. Cutter, and S.J. Barenkamp. 1998. Prevalence and distribution of the *hmw* and *hia* genes and the HMW and Hia adhesins among genetically diverse strains of non–typeable *Haemophilus influenzae*. Infect. Immun. 66:364–368.
St. Geme III, J.W., S. Falkow, and S.J. Barenkamp. 1993. High–molecular–weight proteins of non–typeable *Haemophilus influenzae* mediate attachment to human epithelial cells. Proc. Natl. Acad. Sci. USA 90 : 2875–2879.
Barenkamp, S.J. 1996. Immunization with high–molecular–weight adhesion proteins of non–typeable *Haemophilus influenzae* modifies experimental otitis media in chinchillas. Infect. Immun. 64:1246–1251.

(List continued on next page.)

*Primary Examiner*—Jennifer E. Graser
(74) *Attorney, Agent, or Firm*—Sim & McBurney

(57) ABSTRACT

A multi-valent immunogenic composition confers protection on an immunized host against infection caused by both *Haemophilus influenzae* and *Moraxella catarrhalis*. Such composition comprises at least four antigens comprising at least one antigen from *Haemophilus influenzae*, and at least one antigen from *Moraxella catarrhalis*. Three of the antigens are adhesins. High molecular weight (HMW) proteins and *Haemophilus influenzae* adhesin (Hia) proteins of non-typeable Haemophilus and a 200 kDa outer membrane protein of *Moraxella catarrhalis* comprise the adhesin components while the other antigen is a non-proteolytic analog of Hin47 protein. Each component does not impair the immunogenicity of the others. The multi-valent immunogenic composition may be combined with DTP component vaccines, which may also include non-virulent poliovirus and PRP-T, to provide a component vaccine without impairment of the immunogenic properties of the other antigens.

22 Claims, 18 Drawing Sheets

OTHER PUBLICATIONS

Yang, Y.P., S.M. Loosmore, B. Underdown, and M.H. Klein. 1998. Nasopharyngeal colonization with non–typeable *H. influenzae*, in chinchillas. Infect. Immun. 66:1973–1980.

St. Geme, J.W. and D. Cutter. 1995. Evidence that surface fibrils expressed by *Haemophilus influenzae* type b promote attachment to human epithelial cells. Molec. Microbiol. 15:77–85.

Barenkamp, S.J. and J.W. St. Geme. 1996. Indentification of a second family of high–molecular–weight adhesion proteins expressed by non–typeable *Haemophilus influenzae*. Molec. Microbiol. 19:1215–1223.

St. Geme, J.W., D. Cutter and S.J. Barenkamp. 1996. Characterization of the genetic locus encoding *Haemophilus influenzae* type be surface fibril. J. Bact. 178:6281–6287.

Retzlaff, C., Y. Yamamoto, P.S. Hoffman, H Friedman, and T.W. Klein. 1994. Bacterial heat shock proteins directly induce cytokine MRNA and interleukin–1 secretion in macrophage cultures. Infect. Immun. 62:5689–5693.

Loosmore, S.M., Y–P. Yang, R. Oomen, J.M. Shortreed, D.C. Coleman, and M.H. Klein. 1998. The *Haemophilus influenzea* HtrA protein is a protective antigen. Infect. Immun. 66:899–906.

Holmes, D.S. and Quigley, M. 1981. A rapid boiling method for the preparation of bacterial plasmids. Anal. Biochem. 114:193–197.

Tabor S. and Richardson C.C., 1985. A. bacteriophage T7 RNA polymerase/promoter system for controlled exclusive expression of specific genes. Proc. Natl. Acad. Sci. 82(4): 1074–1078.-

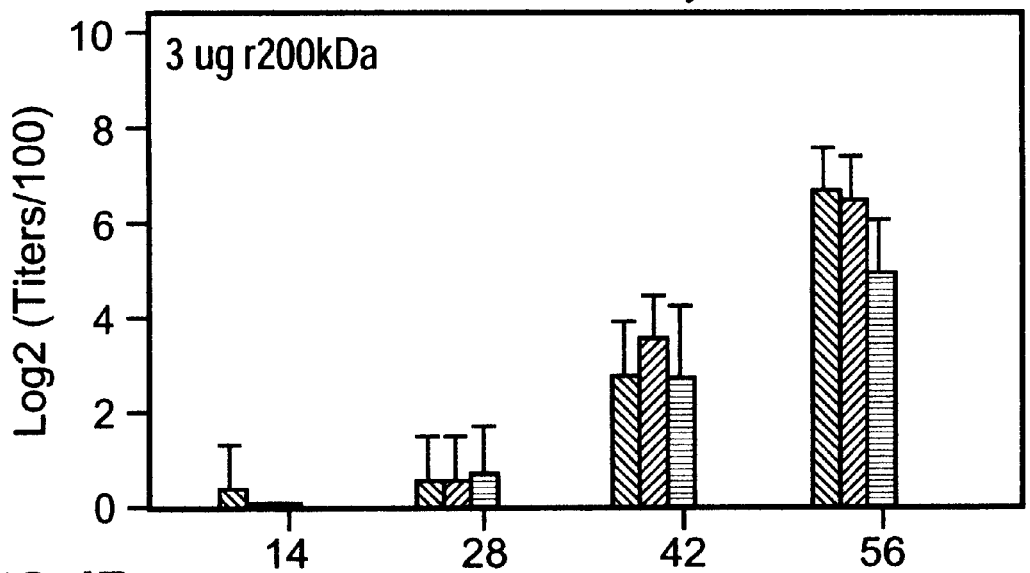
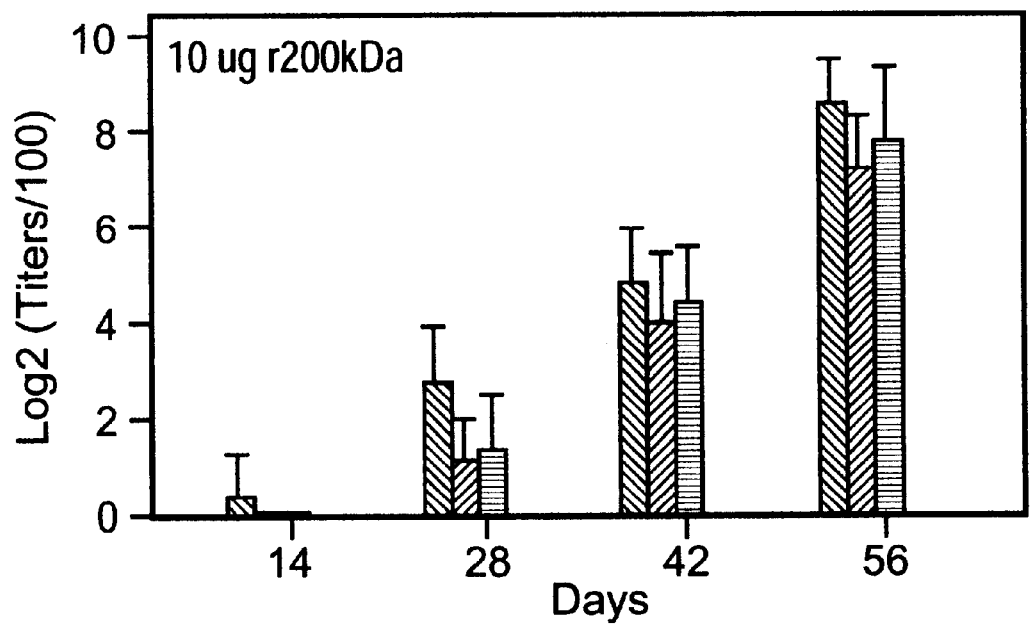

FIG.5A

Anti-H91AHin47 Antibody Titers in Guinea Pigs

25 ug H91A/ rHMW/ rHia

FIG.5B 50 ug H91A/ rHMW/ rHia

Days

- + 0 ug r200 kDa
- + 25 ug r200 kDa
- + 50 ug r200 kDa
- + 100 ug r200 kDa

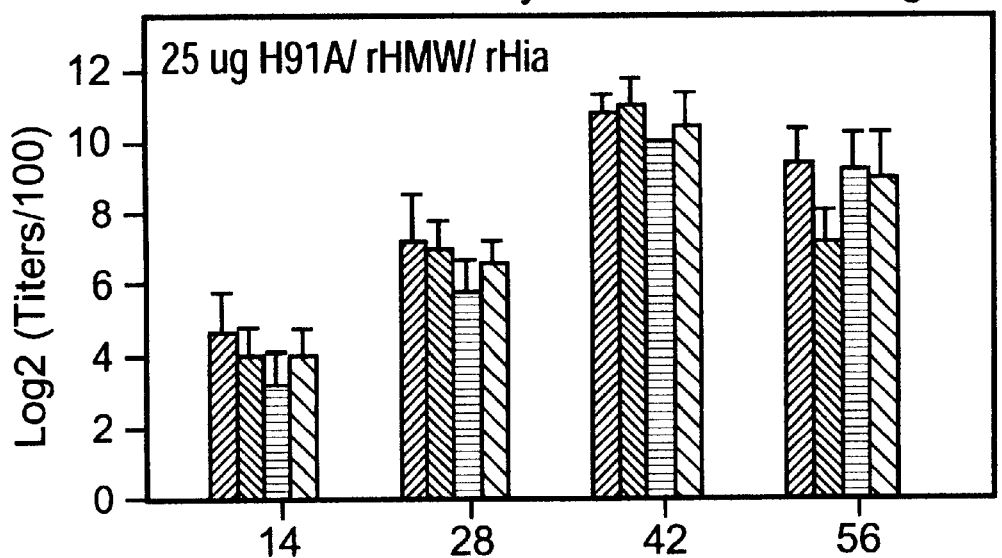
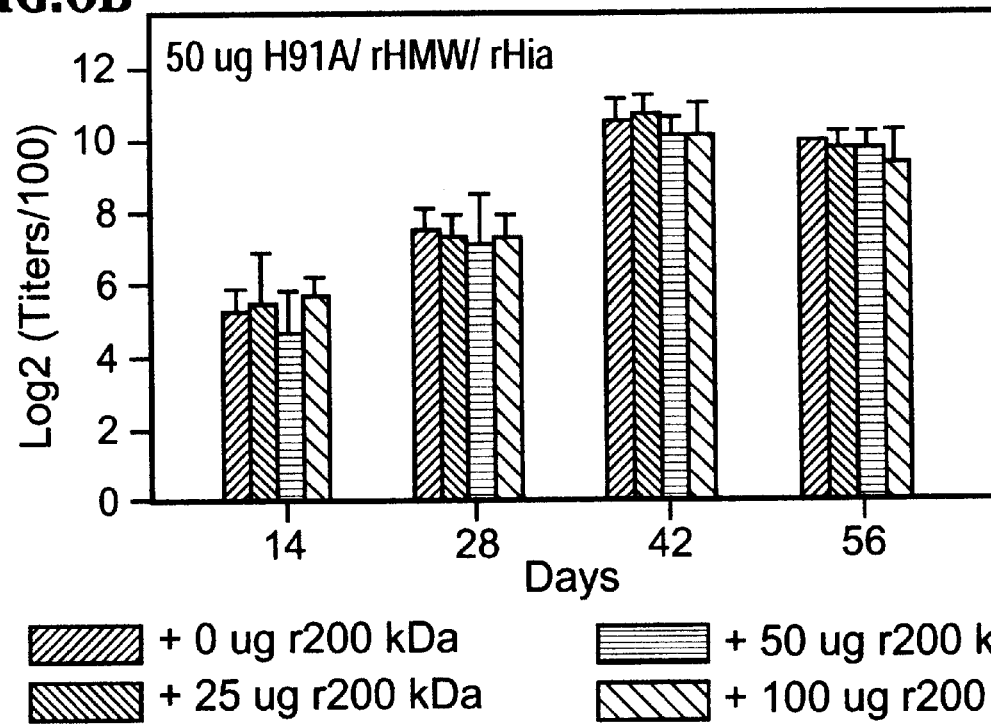

FIG. 7A Anti-rHia Antibody Titers in Guinea Pigs 25 ug H91A/ rHMW/ rHia

FIG. 7B

50 ug H91A/ rHMW/ rHia

Days

+ 0 ug r200 kDa
+ 25 ug r200 kDa
+ 50 ug r200 kDa
+ 100 ug r200 kDa

MULTI-COMPONENT VACCINE TO PROTECT AGAINST DISEASE CAUSED BY *HAEMOPHILUS INFLUENZAE* AND *MORAXELLA CATARRHALIS*

FIELD OF INVENTION

The present invention relates to the field of vaccinology and, in particular, to a multi-component vaccine comprising recombinant proteins from *Haemophilus influenzae* and *Moraxella catarrhalis*.

BACKGROUND TO THE INVENTION

*Haemophilus influenzae* is the cause of several serious human diseases, such as meningitis, epiglottitis, septicemia and otitis media. There are six serotypes of *H. influenzae*, designated a to f, that are identified by their capsular polysaccharide. *H. influenzae* type b (Hib) was a major cause of bacterial meningitis until the introduction of several Hib conjugate vaccines in the 1980's (ref. 1. Throughout the application, various references are referred to in parenthesis to more fully describe the state of the art to which this invention are referred to in parenthesis to more fully describe the state of the art to which this invention pertains. Full bibliographic information for each citation is found at the end of the specification, immediately preceding the claims. The disclosures of these references are hereby incorporated by reference into the present disclosure). Vaccines based upon *H. influenzae* type b capsular polysaccharide conjugated to diphtheria toxoid (ref. 2), tetanus toxoid (ref. 3, and U.S. Pat. No. 4,496,538), or *Neisseria meningitidis* outer membrane protein (ref. 4) have been effective in reducing *H. influenzae* type b-induced meningitis. The other serotypes of *H. influenzae* are associated with invasive disease at low frequencies, although there appears to be an increase in the incidence in disease caused by these strains as the incidence of Hib disease declines (refs. 5, 6). Non-encapsulated or non-typeable *H. influenzae* (NTHi) are also responsible for a wide range of human diseases including otitis media, epiglottitis, pneumonia, and tracheobronchitis. The incidence of NTHi-induced disease has not been affected by the introduction of the Hib vaccines (ref. 7).

Otitis media is the most common illness of early childhood, with 60 to 70% of all children, of less than 2 years of age, experiencing between one and three ear infections (ref. 8). Chronic otitis media is responsible for hearing, speech and cognitive impairments in children. *H. influenzae* infections account for about 30% of the cases of acute otitis media and about 60% of chronic otitis media. *M. catarrhalis* infections account for an additional 15 to 20% of acute otitis media. In the United States alone, treatment of otitis media costs between 1 and 2 billion dollars per year for antibiotics and surgical procedures such as tonsillectomies, adenoidectomies and insertion of tympanostomy tubes. It is estimated that an additional $30 billion is spent per annum on adjunct therapies such as speech therapy and special education classes. *Moraxella (Branhamella) catarrhalis* is the third most common cause of otitis media and sinusitis in children, responsible for 15 to 20% of disease. It has also been associated with lower respiratory tract disease in children and adults, including pneumonia and chronic bronchitis and more rarely it can cause bacteremia and meningitis (refs. 9, 10, 11). There are no vaccines available to protect against *M. catarrhalis* disease. Furthermore, many of the causative organisms of otitis media are becoming resistant to antibiotic treatment. An effective prophylactic vaccine against otitis media is thus highly desirable.

During natural infection, surface-exposed outer membrane proteins that stimulate an antibody response are potentially important targets for bactericidal and/or protective antibodies and therefore potential vaccine candidates. Barenkamp and Bodor (ref. 12) demonstrated that convalescent sera from children suffering from otitis media due to NTHi, contained antibodies to high molecular weight (HMW) proteins. About 70 to 75% of NTHi strains express the HMW proteins and most of these strains contain two gene clusters termed hmw1ABC and hmw2ABC (refs. 13, 14). The HMWA proteins have been demonstrated to be adhesins mediating attachment to human epithelial cells (ref. 15). Immunization with a mixture of native HMW1A and HMW2A proteins resulted in partial protection in the chinchilla intrabulla challenge model of otitis media (ref. 16).

U.S. Pat. No. 5,603,938 (Barenkamp), assigned to St. Louis University and Washington University and the disclosure of which is incorporated herein by reference, describes the cloning, expression and sequencing of the genes encoding the HMW1 and HMW2 proteins from strain 12 of non-typeable Haemophilus. The HMW proteins are a family of proteins from non-typeable Haemophilus of molecular weight of about 120 to 125 kDa which are found in non-typeable Haemophilus strains. The HMW proteins are absent from encapsulated strains of Haemophilus.

The production of native HMW proteins from *H. influenzae* strains is very low and a method for producing protective recombinant HMW (rHMW) proteins has been described in U.S. patent application Ser. No. 09/167,568 filed Oct. 7, 1998, assigned to the assignee hereof and the disclosure of which is incorporated herein by reference. A chinchilla nasopharyngeal colonization model has been developed specifically to demonstrate vaccine efficacy of adhesins (ref. 17) and the rHMW proteins are protective in this model as described in the aforementioned U.S. patent application No. 09/167,568. The rHMW1A and rHMW2A proteins were shown to afford equivalent protection to each other and the rHMW1A protein was chosen for further vaccine studies. In this application, rHMW refers to recombinant HMW1A from NTHi strain 12, although the corresponding recombinant HMW1A protein from other NTHi strains and corresponding rHMW2A protein from NTHi strains may be employed. The corresponding naturally-occurring proteins may be employed.

A second family of high molecular weight adhesion proteins has been identified in about 25% of NTHI and in encapsulated *H. influenzae* strains (refs. 18, 19, 20). U.S. Pat. No. 5,646,259 (St. Geme, III et al), assigned to St. Louis University and Washington University, and the disclosure of which is incorporated herein by reference, describes the cloning, expression and sequences of genes encoding what are termed therein the HA1 and HA2 proteins, which have limited homology to the HMW1 and HMW2 proteins of U.S. Pat. No. 5,603,938.

The NTHi member of this second family is termed *Haemophilus influenzae* adhesin or Hia (HA1) and the homologous protein found in encapsulated strains is termed *Haemophilus influenzae* surface fibril protein or Hsf (HA2). The hia gene was originally cloned from an expression library using convalescent sera from an otitis media patient, which indicates that it is an important immunogen during disease. The prototype Hia and Hsf proteins demonstrate about 82% sequence similarity, although the Hsf protein is considerably larger. The proteins are comprised of conserved amino and carboxy termini and several repeat motifs, with Hsf containing more repeat sequences than Hia.

U.S. patent application Ser. No. 09/268,347 filed Mar. 16, 1999 (1038–860), assigned to the assignee hereof and the disclosure of which is incorporated herein by reference, describes the production of full-length and N-terminally truncated versions of the Hia protein (rHia) in *E. coli*. These recombinant proteins have been demonstrated to protect against bacteremia caused by *H. influenzae* type a and type b organisms, and to confer partial protection against nasopharyngeal colonization by non-typeable *H. influenzae*. In this application, rHia refers to V38 rHia from NTHi strain 11, although other recombinant full-length and N-terminally truncated Hia proteins from other NTHi strains may be employed. Corresponding naturally-occurring proteins also may be employed.

A high molecular weight adhesin identified in *M. catarrhalis*, has been termed 200 kDa and is described in U.S. Pat. No. 5,808,024 (Sasaki et al), assigned to the assignee hereof and the disclosure of which is incorporated herein by reference, as well as copending U.S. application Ser. No. 08/621,944 filed Mar. 26, 1996 (WO 96/34960), assigned to the assignee hereof and the disclosure of which is incorporated herein by reference. The 200 kDa protein has been identified in 96 out of 109 *M. catarrhalis* strains, including 73 out of 74 otitis media-derived strains, and is postulated to be a virulence factor. There is sequence homology between the *M. catarrhalis* 200 kDa protein and the *H. influenzae* Hia and Hsf proteins. In addition, anti-native 200 kDa antibody recognized the rHia protein on an immunoblot, indicating antigenic relatedness, as demonstrated in the aforementioned copending U.S. patent application Ser. No. 09/268,347 (1038–860).

There is no suitable animal model for *M. catarrhalis* infection and disease, but a bactericidal antibody assay has been developed as a surrogate assay, as described in the aforementioned U.S. Pat. No. 5,808,024. An N-terminally truncated V56 r200 kDa protein has been expressed in *E. coli* and antibody raised to V56 r200 kDa has been shown to be bactericidal against homologous and heterologous strains of *M. catarrhalis*, thus indicating its usefulness as a vaccine antigen, as described in copending U.S. patent application Ser. No. 09/361,619 filed Jul. 27, 1999, assigned to the assignee hereof and the disclosure of which is incorporated herein by reference. In this application, r200 kDa refers to the V56 r200 kDa protein from *M. catarrhalis* strain 4223, although other recombinant full-length and N-terminally truncated 200 kDa proteins from other *M. catarrhalis* strains may be employed. Corresponding naturally-occurring proteins also may be employed.

When under environmental stress, such as high temperature, organisms overproduce stress response or heat shock proteins (hsps). Bacterial hsps have been shown to be important immunogens, stimulating both B cells and T cells (Ref. 21). The bacterial HtrA or DegP heat shock proteins are expressed under conditions of stress and the *H. influenzae* HtrA or Hin47 protein has been shown to be a partially protective antigen in the intrabulla challenge model of otitis media (ref. 22). The HtrA proteins are serine proteases and their proteolytic activity makes them unstable. In addition, as components of a multi-component vaccine, the wild-type HtrA protein will degrade admixed antigens. The site-directed mutagenesis of the *H. influenzae* htrA gene (termed hin47) and the properties of the mutants have been fully described in U.S. Pat. No. 5,506,139 (Loosmore et al), assigned to the assignee hereof and the disclosure of which is incorporated herein by reference.

U.S. Pat. No. 5,506,139 (Loosmore et al) describes the preparation of analogs of *Haemophilus influenzae*Hin47 protein which have a decreased protease activity which is less than about 10% of that of the natural Hin47 protein and which preferably have substantially the same immunogenic properties as natural Hin47 protein. The patent also describes the isolation, purification and characterization of nucleic acid molecules encoding the Hin47 analogs. The natural Hin47 protein is immunologically conserved among non-typeable and encapsulated isolates of *H. influenzae*. The amino acid sequence of the natural Hin47 protein and the nucleotide sequence of the encoding hin47 gene are described in WO 94/00149 published Jan. 6, 1994 and incorporated herein by reference.

The Hin47 analogs of U.S. Pat. No. 5,506,139 are prepared by deleting or replacing by a different amino acid at least one amino acid of the natural Hin47 contributing to protease activity or by inserting at least one amino acid into the natural Hin47 protein, as specifically described therein. The at least one deleted or replaced amino acid may be selected from amino acids 195 to 201 of Hin47 and specifically may be Serine-197, which may be deleted or replaced by alanine. In addition, the at least one deleted or replaced amino acid may be His-91 and may be deleted or replaced by alanine, lysine or arginine. Furthermore the at least one deleted or replaced amino acid may be Asp-121 and may be deleted or replaced by alanine.

In copending U.S. patent application Ser. No. 08/487,167 filed Jun. 7, 1995 (now U.S. Pat. No. 5,869,302), assigned to the assignee hereof and the disclosure of which is incorporated herein by reference, there are described multiple mutations effected at different amino acids of the natural Hin47 protein to provide the non-proteolytic Hin47 analog.

In the present invention, the mutation of histidine 91 to alanine (sometimes termed herein "H91A") is employed as illustration of the mutant Hin47 protein, although other Hin47 mutants with reduced protease activity as described in the aforementioned patent and application may be used.

The non-proteolytic HtrA analogue, H91A Hin47, has been shown to be a protective antigen against bacteremia caused by *H. influenzae* type b and against otitis media caused by non-typeable *H. influenzae* (ref. 22). HtrA was found in all *H. influenzae* strains examined, including encapsulated strains. There was also evidence of cross-reactivity with a specific protein from *M. catarrhalis* on immunoblot, suggesting the possibility of an HtrA analogue in this organism.

The main goal of a prophylactic vaccine against otitis media is to prevent the establishment of nasopharyngeal colonization by including adhesins as immunogens. The *H. influenzae* HMW and Hia proteins are adhesins that have been shown to prevent colonization. However, since there may be a small percentage of *H. influenzae* strains that do not contain the hmw or hia genes, the H91A Hin47 antigen has been added to provide protection against such strains, although any other non-proteolytic analog of Hin47 may be employed. The addition of one or more *M. catarrhalis* 200 kDa adhesins provides protection against colonization by this organism. The present invention provides for a multi-component vaccine to protect against colonization and disease caused by encapsulated or unencapsulated *H. influenzae* and *M. catarrhalis* organisms.

It would be desirable to provide efficacious combination vaccines comprising *H. influenzae* and *M. catarrhalis* components containing selected relative amounts of selected antigens.

SUMMARY OF THE INVENTION

The present invention is directed towards the provision of a multi-component vaccine, comprising at least three antigens from *H. influenzae* and at least one antigen from *M. catarrhalis*, to protect against disease caused by *H. influenzae* and *M. catarrhalis*, including otitis media.

In accordance with one aspect of the present invention, there is provided a multi-valent immunogenic composition for conferring protection in a host against disease caused by infection with *Haemophilus influenzae* and *Moraxella catarrhalis*, which comprises at least four different antigens, comprising at least one antigen from *Haemophilus influenzae* and at least one antigen from *Moraxella catarrhalis*, at least three of which antigens are adhesins and at least one of which adhesins is from *Moraxella catarrhalis*.

One of the antigens which is an adhesin may be a high molecular weight protein (HMW) of a non-typeable strain of Haemophilus, particularly an HMW1 or HMW2 protein of the non-typeable strain, which may be produced recombinantly.

Another of the antigens which is an adhesin may be a *Haemophilus influenzae* adhesin (Hia) protein of a non-typeable strain of *Haemophilus influenzae* or a *Haemophilus influenzae* surface fibril (hsf) protein of a typeable strain of *Haemophilus influenzae*, which may be produced recombinantly.

An antigen of *Haemophilus influenzae* which is not an adhesin may be a non-proteolytic heat shock protein of a strain of *Haemophilus influenzae*, which may be an analog of *Haemophilus influenzae* Hin47 protein having a decreased protease activity which is less than about 10% of that of natural Hin47 protein.

One of the antigens which is an adhesin may be an outer membrane protein of *Moraxella catarrhalis* having an apparent molecular mass of about 200 kDa, as determined by SDS-PAGE, and may be produced recombinantly.

In accordance with a preferred embodiment of the present invention, there is provided a multi-valent immunogenic composition for conferring protection in a host against disease caused by both *Haemophilus influenzae* and *Moraxella catarrhalis*, which comprises: (a) an analog of *Haemophilus influenzae* Hin47 protein having a decreased protease activity which is less than about 10% of natural Hin47 protein, (b) a *Haemophilus influenzae* adhesin (Hia) protein of a non-typeable strain of *Haemophilus influenzae*, (c) a high molecular weight (HMW) protein of a strain of non-typeable *Haemophilus influenzae*, and (d) an outer membrane protein of *Moraxella catarrhalis* having an apparent molecular mass of about 200 kDa, as determined by SDS-PAGE.

In such composition, the Hin47, Hia, HMW and 200 kDa proteins may be present in amounts which do not impair the individual immunogenicities of the proteins, so that there is no interference between the components with respect to their individual immunogenicities.

The analog of Hin47 protein may be one in which at least one amino acid of the natural Hin47 protein contributing to protease activity has been deleted or replaced by a different amino acid and which has substantially the same immunogenic properties as natural Hin47 protein.

Such at least one amino acid may be selected from the group consisting of amino acids 91, 121 and 195 to 207 of natural Hin47 protein. Specific mutants which may be used including serine-197 replaced by alanine, Histidine-91 replaced by alanine, lysine or arginine and Asp-121 replaced by alanine.

The HMW protein of the non-typeable strain of *Haemophilus influenzae* may be a HMW1 or HMW2 protein and may be recombinantly produced. The HMW1 and HMW2 proteins are derived from the respective strains of non-typeable *Haemophilus influenzae* and possess respective molecular weights as set forth in the following Table I:

TABLE I

| Molecular Weight (kDa) | | Non-typeable *H. influenzae* Strain | | | | |
| --- | --- | --- | --- | --- | --- | --- |
| | | 12 | JoyC | K21 | LCDC2 | PMH1 | 15 |
| Mature Protein: | HMW1 | 125 | 125.9 | 104.4 | 114.0 | 102.4 | 103.5 |
| | HMW2 | 120 | 100.9 | | 111.7 | 103.9 | 121.9 |

The Hia and 200 kDa proteins may be produced recombinantly and may comprise N-terminal truncations, V38 rHia and V56 r200 kDa respectively.

The immunogenic composition of the invention may be further formulated with an adjuvant. Such adjuvant for use in the present invention may include (but not limited to) aluminum phosphate, aluminum hydroxide, QS21, Quil A, derivatives and components thereof, ISCOM matrix, calcium phosphate, calcium hydroxide, zinc hydroxide, a glycolipid analog, an octadecyl ester of an amino acid, a muramyl dipeptide, polyphosphazene, ISCOPREP, DC-chol, DDBA and a lipoprotein and other adjuvants. Advantageous combinations of adjuvants are described in copending U.S. patent applications Ser. No. 08/261,194 filed Jun. 16, 1994 and 08/483,856 filed Jun. 7, 1995, assigned to the assignee hereof and the disclosures of which are incorporated herein by reference (WO 95/34308, published Nov. 21, 1995). The adjuvant preferably may comprise aluminum phosphate or aluminum hydroxide (collectively known as alum).

The components of the composition may be present in appropriate quantities to provide the desired immune response. The components may be formulated as a vaccine for in vivo administration to the host. The vaccine composition may comprises:

(a) about 25 to about 100 µg of the Hin47 protein analog,
(b) about 25 to about 100 µg of the Hia protein,
(c) about 25 to about 100 µg of the HMW protein, and
(d) about 25 to about 100 µg of the 200 kDa protein.

The immunogenic compositions may be formulated with other antigenic components to provide a multi-valent vaccine in which the additional antigenic component(s) confer protection against disease caused by another pathogen(s). Such additional antigens should be such that and be present in quantities that the immunogenicity of the individual components of the resulting vaccine is not impaired by other individual components of the composition. Such additional antigens preferably are purified antigens in defined quantities to produce a component vaccine.

Such additional antigens may be those traditionally found in multi-valent protective vaccines, such as diphtheria toxoid, tetanus toxoid and pertussis antigens, including pertussis toxoid, filamentous hemagglutinin, pertactin and/ or agglutinogens.

The resulting multi-valent vaccine also may contain non-virulent poliovirus, such as inactivated poliovirus, which may be type 1, type 2 and/or type 3 poliovirus. The multi-component vaccine further may comprise a conjugate of a tetanus or diphtheria toxoid and a capsular polysaccharide of *Haemophilus influenzae*, preferably PRP-T.

The invention extends to a method of immunizing a host against disease caused by infection with both *Haemophilus influenzae* and *Moraxella catarrhalis*, including otitis media, which comprises administering to the host an immunoeffective amount of the immunogenic composition provided herein.

Advantages of the present include a multi-valent vaccine that can confer protection against encapsulated and unencapsulated *Haemophilus influenzae* and *Moraxella catarrhalis* diseases in a safe and efficacious manner.

BRIEF DESCRIPTION OF DRAWINGS

The present invention will be further understood from the following description with reference to the drawings, in which:

In FIG. 1A, the H91A Hin47+rHMW+rHia components were at a concentration of 0.3 μg each and, in FIG. 1B, they were at a concentration of 3.0 μg each. Increasing amounts of r200 kDa were added at 0, 0.3, 1.0, 3.0 and 10.0 μg;

In FIG. 2A, the H91A Hin47+rHMW+rHia components were at a concentration of 0.3 μg each and, in FIG. 2B, they were at a concentration of 3.0 μg each. Increasing amounts of r200 kDa were added at 0, 0.3, 1.0, 3.0 and 10.0 μg;

In FIG. 3A, the H91A Hin47+rHMW+rHia components were at a concentration of 0.3 μg each and, in FIG. 3B, they were at a concentration of 3.0 μg each. Increasing amounts of r200 kDa were added at 0, 0.3, 1.0, 3.0 and 10.0 μg;

FIGS. 4a, 4B, 4C and 4D show the anti-r200 kDa immune responses for H91A Hin47+rHMW+rHia+r200 kDa combination vaccines in mice. In FIG. 4A increasing amounts of H91A Hin47+rHMW+ rHia at 0, 0.3 or 3.0 μg each were added to 0.3 μg of r200 kDa. In FIG. 4B, increasing amounts of H91A Hin47+rHMW+ rHia at 0, 0.3 or 3.0 μg each were added to 1.0 μg of r200 kDa. In FIG. 4C, increasing amounts of H91A Hin47+rHMW+ rHia at 0, 0.3 or 3.0 μg each were added to 3.0 μg of r200 kDa. In FIG. 4D, increasing amounts of H91A Hin47+rHMW+ rHia at 0, 0.3 or 3.0 μg each were added to 10.0 μg of r200 kDa;

FIGS. 5A and 5B show the anti-H91A Hin47 immune responses for H91A Hin47+rHMW+rHia+r200 kDa combination vaccines in guinea pigs. In FIG. 5A, the H91A Hin47+rHMW+rHia components were at a concentration of 25 μg each and, FIG. 5B, they were at a concentration of 50 μg each. Increasing amounts of r200 kDa were added at 0, 25, 50 and 100 μg;

FIGS. 6A and 6B show the anti-HMW immune responses for H91A Hin47+rHMW+rHia+r200 kDa combination vaccines in guinea pigs. In FIG. 6A, the H91A Hin47+rHMW+rHia components were at a concentration of 25 μg each and, in FIG. 6B, they were at a concentration of 50 μg each. Increasing amount of r200 kDa were added at 0, 25, 50 and 100 μg;

FIGS. 7A and 7B show the anti-Hia immune responses for H91A Hin47+rHMW+rHia+r200 kDa combination vaccines in guinea pigs. In FIG. 7A, the H91A Hin47+rHMW+rHia components were at a concentration of 25 μg each and in FIG. 7B, they were at a concentration of 50 μg each. Increasing amounts of r200 kDa were added at 0, 25, 50 and 100 μg;

In FIG. 8A, increasing amounts of H91A Hin47+rHMW+ rHia at 0, 25 or 50 μg each were added to 25 μg of r200 kDa. In FIG. 8B, increasing amounts of H91A Hin47+rHMW+ rHia at 0, 25 or 50 μg each were added to 50 μg of r200 kDa. In FIG. 8C, increasing amounts of H91A Hin47+rHMW+ rHia at 0, 25 or 50 μg each were added to 100 μg of r200 kDa;

GENERAL DESCRIPTION OF THE INVENTION

Figure 1A:
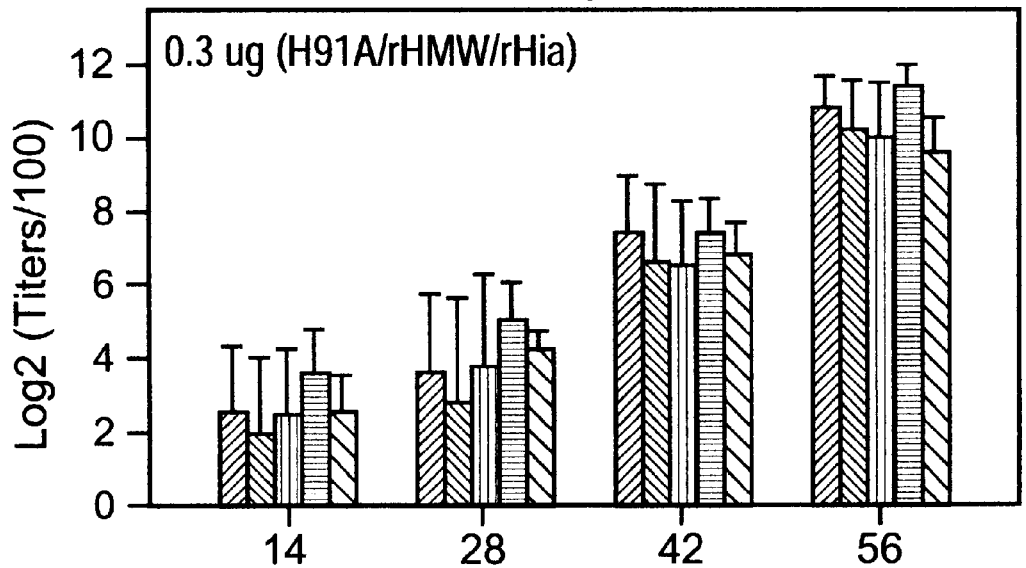
FIGS. 1A and 1B show the anti-H91A Hin47 immune responses for H91A Hin47+rHMW+rHia +r200 kDa combination vaccines in mice.

The production and purification of recombinant *H. influenzae* antigens rHMW, rHia and H91A Hin47 have been fully described in the aforementioned U.S. patent applications Ser. Nos. 09/167,568 and 09/268,347 and the aforementioned U.S. Pat. No. 5,506,139 respectively. The production and purification of recombinant *M. catarrhalis* r200 kDa antigen has been fully described in the aforementioned U.S. patent application Ser. No. 09/361,619.

Colonization of the nasopharynx is the first step in disease development for many bacterial or viral pathogens and vaccines containing adhesin molecules should protect against this first step in disease progression. The high molecular weight (HMW) proteins, found in approximately 75% of non-typeable *H. influenzae*, have been shown to be adhesins that are protective against colonization when administered in a vaccine composition. The HMW proteins are not present in encapsulated *H. influenzae* strains or in about 25% of non-typeable *H. influenzae* strains, thus they are not sufficient for a fully-effective vaccine having strain-wide protectivity.

The Hia/Hsf proteins also have been shown to be adhesins and are present in all encapsulated *H. influenzae* strains and in the majority of those non-typeable *H. influenzae* strains that do not produce HMW proteins. The rHia protein is protective against colonization by NTHi and against bacteremia caused by *H. influenzae* type a and type b organisms. There is a small percentage of NTHi strains that produce neither HMW nor Hia proteins.

The HtrA protein or Hin47 is found in all encapsulated and non-typeable *H. influenzae* strains. Hin47 or its non-proteolytic H91A Hin47 mutant, is protective against bacteremia caused by *H. influenzae* type b and otitis media caused by non-typeable *H. influenzae*, but it does not prevent colonization. Hin47 is proteolytic and cannot itself be used in protein formulations. A combination vaccine comprising rHMW, rHia and H91A Hin47 antigens may be formulated to protect against *H. influenzae* disease, including otitis media.

The *M. catarrhalis* 200 kDa protein is genetically and antigenically related to the Hia/Hsf family of adhesins. Immunization with r200 kDa protein elicits cross-reactive bactericidal antibodies. A combination vaccine comprising the three *H. influenzae* antigens and the *M. catarrhalis* r200 kDa protein may be formulated to protect against *H. influenzae* and *M. catarrhalis* disease, including otitis media.

The composition of multi-component vaccines is important. The vaccine components must be compatible and they must be combined in appropriate ratios to avoid antigenic interference and optimize any possible synergies. If administered with other established vaccines, they must not interfere with the protection afforded by the vaccine against other disease(s).

The preparation, immunogenic and protective properties of a three component rHMW+rHia+H91A Hin47 vaccine have been described in U.S. patent application Ser. No. 09/261,182 filed Mar. 3, 1999, assigned to the assignee hereof and the disclosure of which is incorporated herein by reference. As described therein, rHia is combined with a two component rHMW+H91A Hin47 vaccine, the preparation, immunogenic and protective properties of which are described in copending U.S. application Ser. No. 09/210,995 filed Dec. 15, 1998, assigned to the assignee hereof and the disclosure of which is incorporated herein by reference.

Various antigen ratios were compared for the four component H91A Hin47+rHMW+rHia+r200 kDa vaccine and the immunogenicity was compared in two animal species. In mice, the addition of the r200 kDa component to the low dose three component vaccine (0.3 μg each), enhanced the primary anti-H91A Hin47 response, however the response for the higher dose vaccine (3.0 μg each), was not affected. In guinea pigs, the anti-H91A Hin47 response for the 3 or 4 component vaccine was equivalent. In mice the anti-rHMW response to the low dose three component vaccine with or without added r200 kDa antigen was very poor. There did not appear to be either a synergistic or inhibiting effect on the anti-rHMW response upon addition of the r200 kDa component to the high dose vaccine. There was no apparent effect on the anti-rHia response upon addition of the r200 kDa component to the low or high dose three component vaccine. The immune response to the r200 kDa component with or without the added three component vaccine, was generally poorer than observed for the other components. At the 1.0 μg dose of r200 kDa, the addition of the three component vaccine at 3 μg each, decreased the immune response to r200 kDa. However, at higher doses, the anti-r200 kDa response was unaffected by the presence of the other components. In guinea pigs, the immune response to each antigen were unaffected by the presence of the other three.

The protection afforded by the four component vaccine was assessed in the chinchilla model of nasopharyngeal colonization. The animals were well protected against colonization, at levels equivalent to a mono-component rHMW vaccine, a two component rHMW+H91A Hin47 vaccine, or a three component rHMW+rHia+H91A Hin47 vaccine. The protection afforded by the four component vaccine was also assessed in the chinchilla intrabulla challenge model of otitis media. The animals were partially protected against otitis media, at levels equivalent to a mono-component H91A Hin47 vaccine, a two-component H91A Hin47+rHMW vaccine, or a three-component H91A Hin47+rHMW+rHia vaccine. These data demonstrate that the addition of more antigens to the vaccine has not had a deleterious effect on the protection afforded by a single component.

Figure 1B:
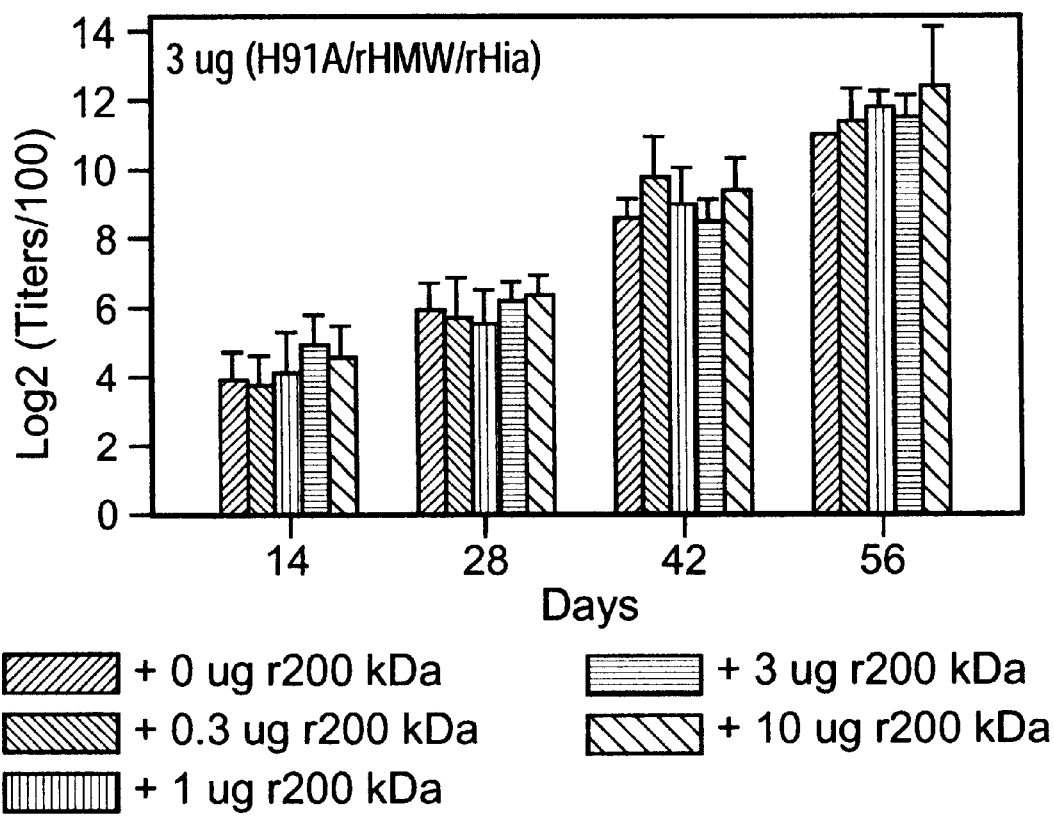

Referring to FIGS. 1A and 1B, there is illustrated the immune response in mice, to the H91A Hin47 antigen of a three or four component vaccine in which the H91A Hin47+rHMW+rHia components are fixed at 0.3 or 3.0 μg each and r200 kDa is added at concentrations of 0, 0.3, 1.0, 3.0 and 10.0 μg. High titer antibodies are obtained in the final bleed sera for all combinations.

Figure 2A:
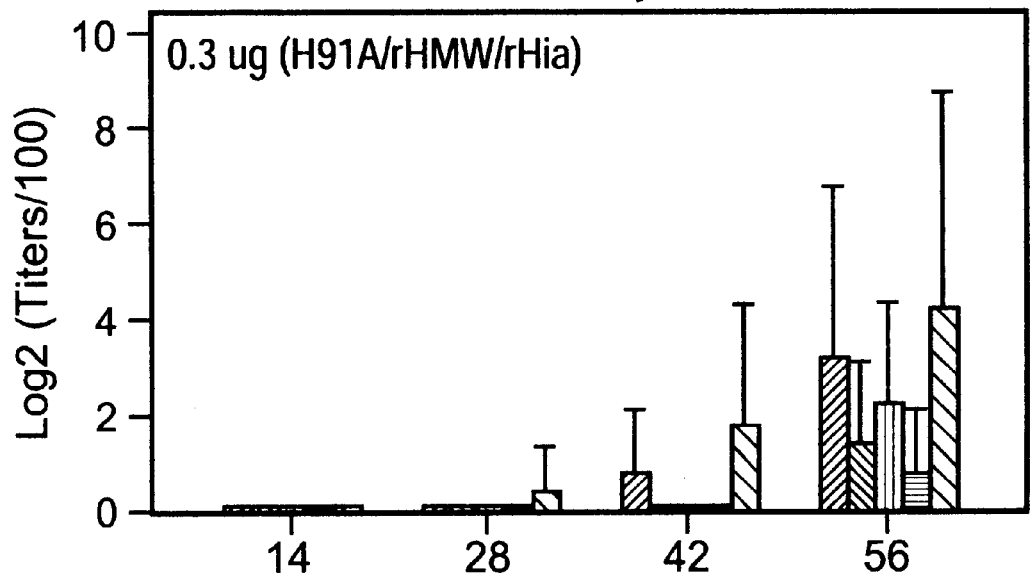
FIGS. 2A and 2B show the anti-rHMW immune responses for H91A Hin47+rHMW+rHia+r200 kDa combination vaccines in mice.
Figure 2B:
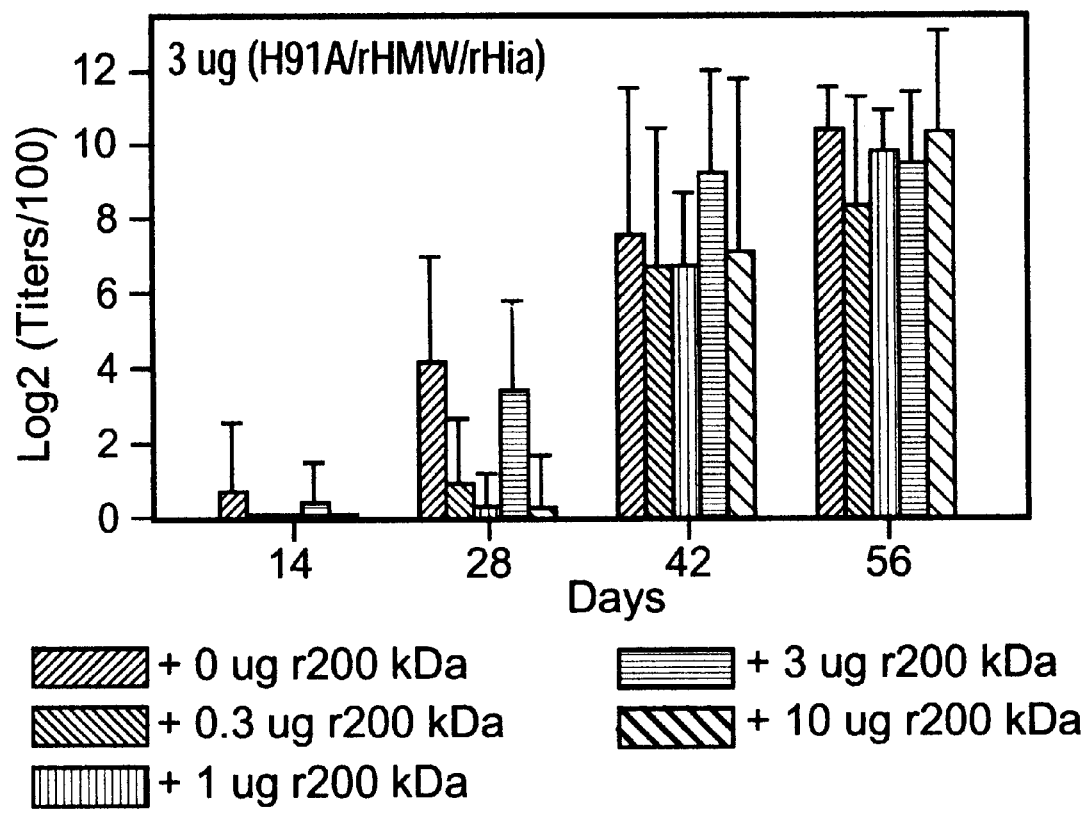

Referring to FIGS. 2A and 2B, there is illustrated the immune response in mice, to the rHMW antigen of a three or four component vaccine in which the H91A Hin47+rHMW+rHia components are fixed at 0.3 or 3.0 μg each and r200 kDa is added at concentrations of 0, 0.3, 1.0 3.0 and 10.0 μg. The immune response to the low dose vaccine is very poor, but high antibody titers are obtained in the final bleed sera for the high dose three or four component vaccines.

Figure 3A:
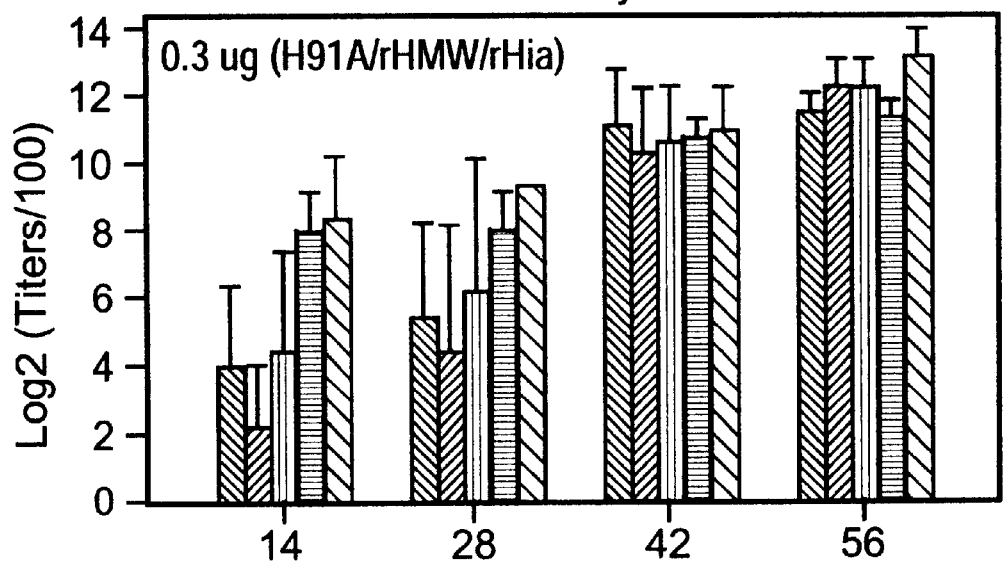
FIGS. 3A and 3B show the anti-rHia immune responses for H91A Hin47+rHMW+rHia+r200 kDa combination vaccines in mice.
Figure 3B:
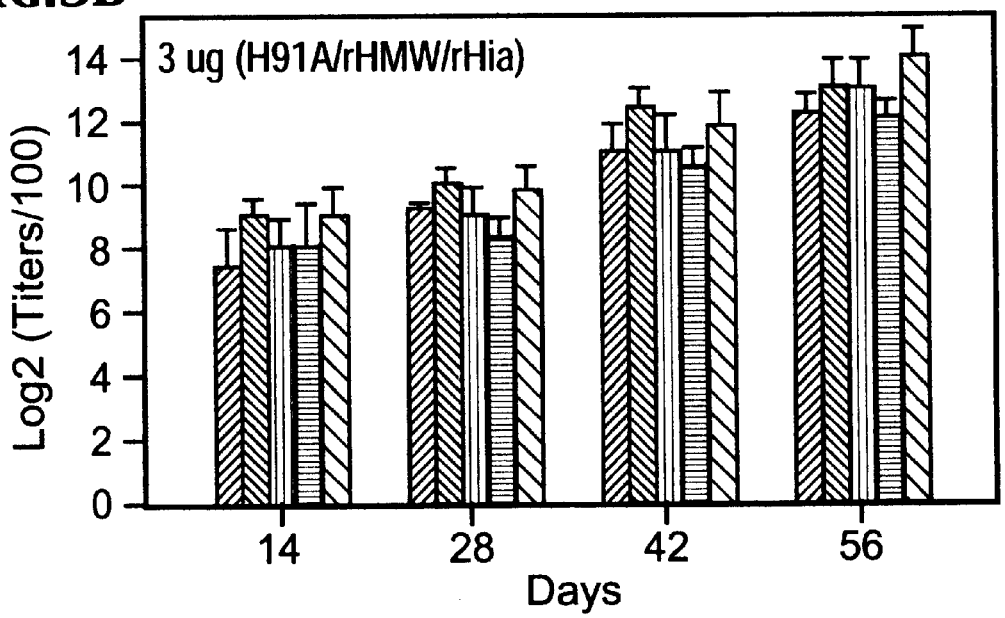
Figure 4A:
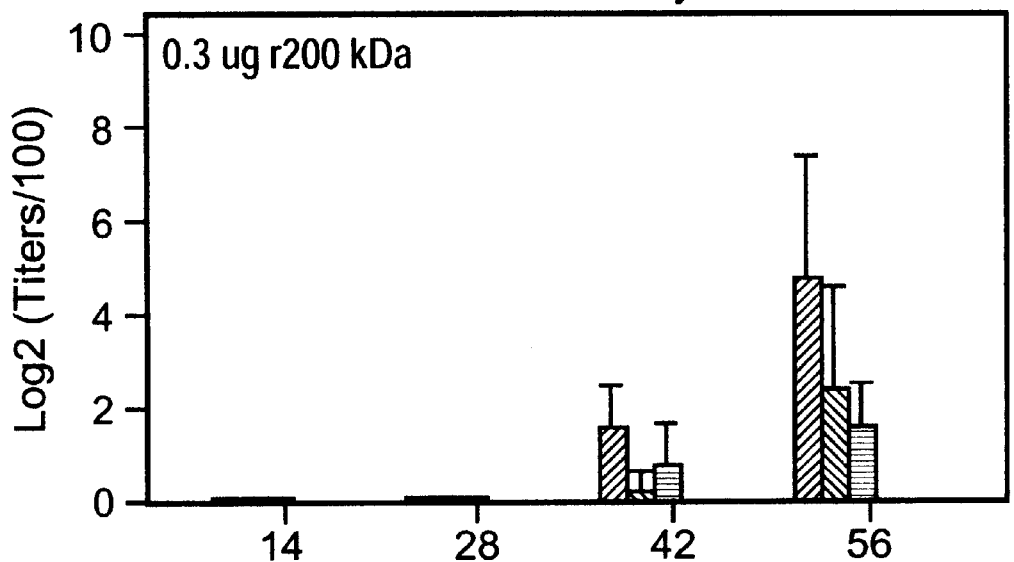
Figure 4B:
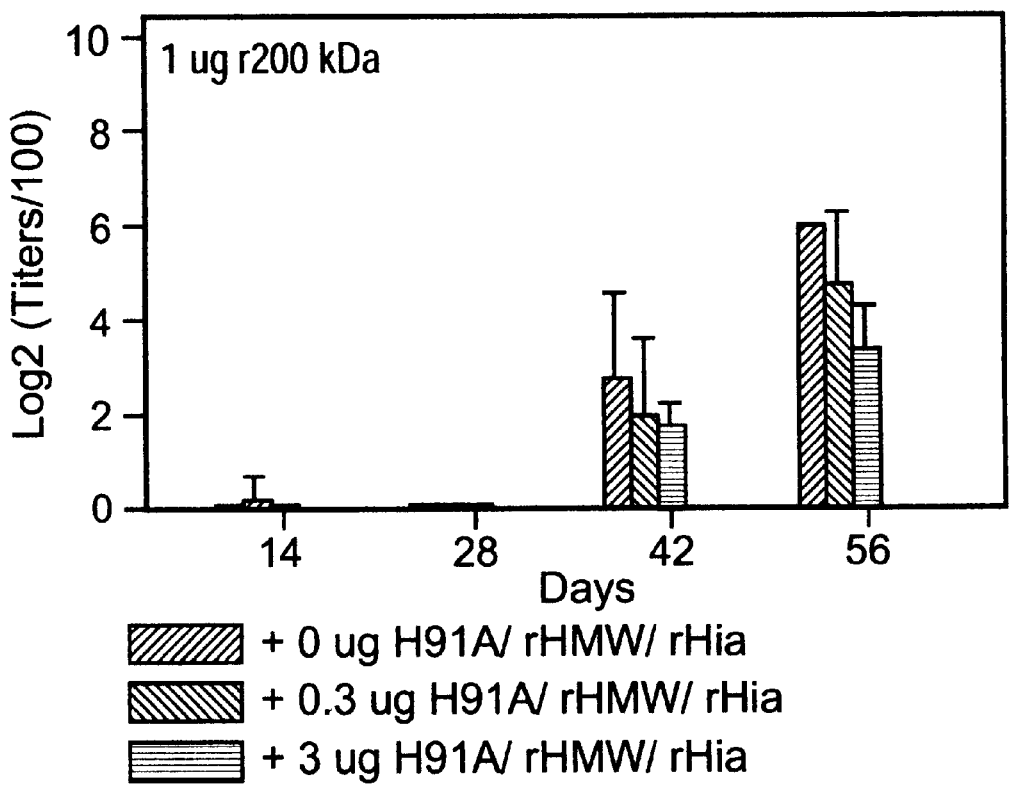

Referring to FIGS. 3A and 3B, there is illustrated the immune response in mice, to the rHia antigen of a three or four component vaccine in which the H91A Hin47+rHMW+rHia components are fixed at 0.3 or 3.0 μg each and r200 kDa is added at concentrations of 0, 0.3, 1.0, 3.0 and 10.0 μg. High titer antibodies are obtained in the final bleed sera for all combinations.

Referring to FIGS. 4A, 4B, 4C and 4D, there is illustrated the immune response in mice, to the r200 kDa antigen of a one or four component vaccine in which the H91A Hin47+rHMW+rHia components are fixed at 0, 0.3 or 3.0 μg each and r200 kDa is added at concentrations of 0.3, 1.0, 3.0 and 10.0 μg. The immune response to the r200 kDa component is very poor at the 0.3 μg and 1.0 μg doses. At the higher doses of 3 or 10 μg of r200 kDa, high antibody titers are obtained for the final bleed sera, irrespective of the presence or absence of the other components.

Referring to FIGS. 5A and 5B, there is illustrated the immune response in guinea pigs, to the H91A Hin47 antigen of a three or four component vaccine in which the H91A Hin47+rHMW+rHia components are fixed at 25 or 50 μg each and r200 kDa is added at concentrations of 0, 25, 50 or 100 μg. High titer antibodies are obtained in the final bleed sera from all combinations.

Referring to FIGS. 6A and 6B, there is illustrated the immune response in guinea pigs, to the rHMW antigen of a three or four component vaccine in which the H91A Hin47+ rHMW+rHia components are fixed at 25 or 50 μg each and r200 kDa is added at concentrations of 0, 25, 50 or 100 μg. High titer antibodies are obtained in the final bleed sera from all combinations.

Referring to FIGS. 7A and 7B, there is illustrated the immune response in guinea pigs, to the rHia antigen of a three or four component vaccine in which the H91A Hin47+ rHMW+rHia components are fixed at 25 or 50 μg each and r200 kDa is added at concentrations of 0, 25, 50 or 100 μg. High titer antibodies are obtained in the final bleed sera from all combinations.

Figure 8A:
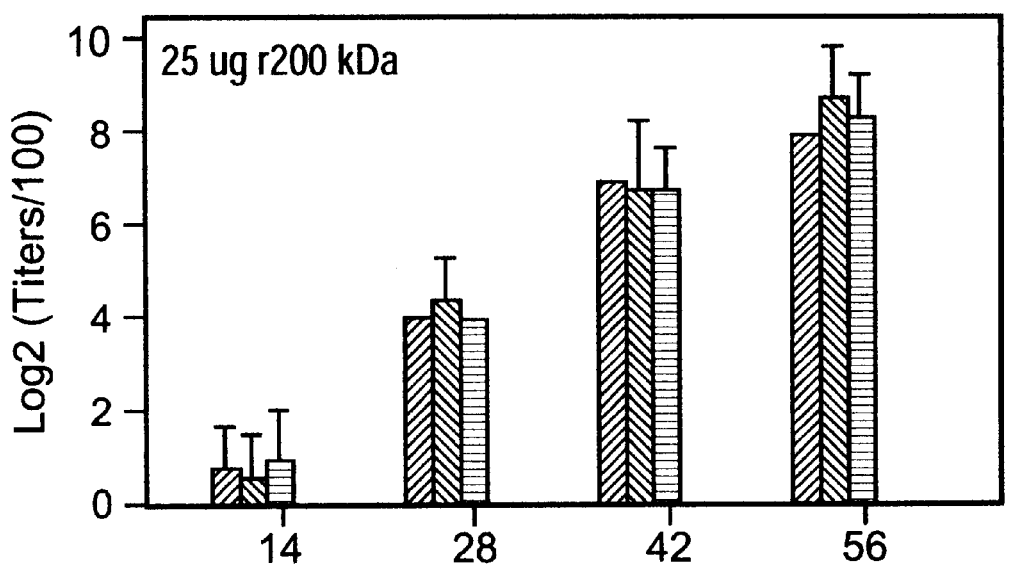
FIGS. 8A, 8B and 8C show the anti-200 kDa immune responses for H91A Hin47+rHMW+rHia+r200 kDa combination vaccines in guinea pigs.
Figure 8B:
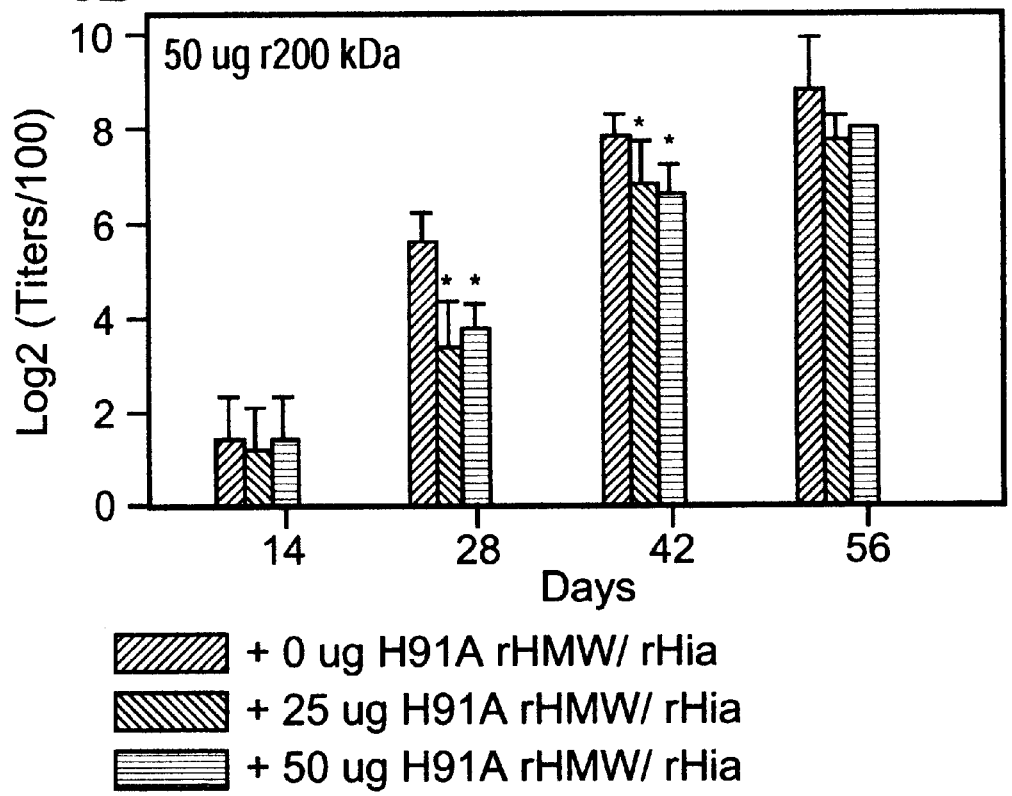
Figure 8C:
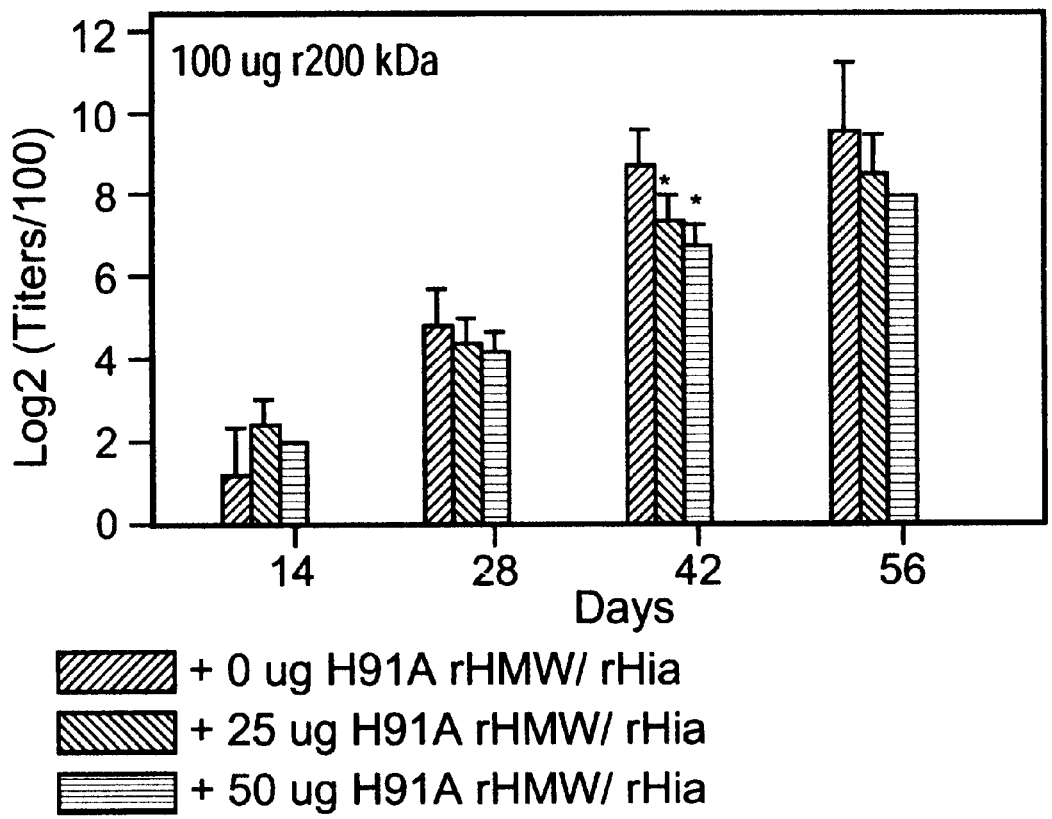

Referring to FIGS. 8A, 8B and 8C, there is illustrated the immune response in guinea pigs, to the r200 kDa antigen of a one or four component vaccine in which the H91A Hin47+rHMW+rHia components are fixed at 0, 25 or 50 μg each and r200 kDa is added at concentrations of 25, 50 or 100 μg. High titer antibodies are obtained in the final bleed sera from all vaccines.

Figure 9:
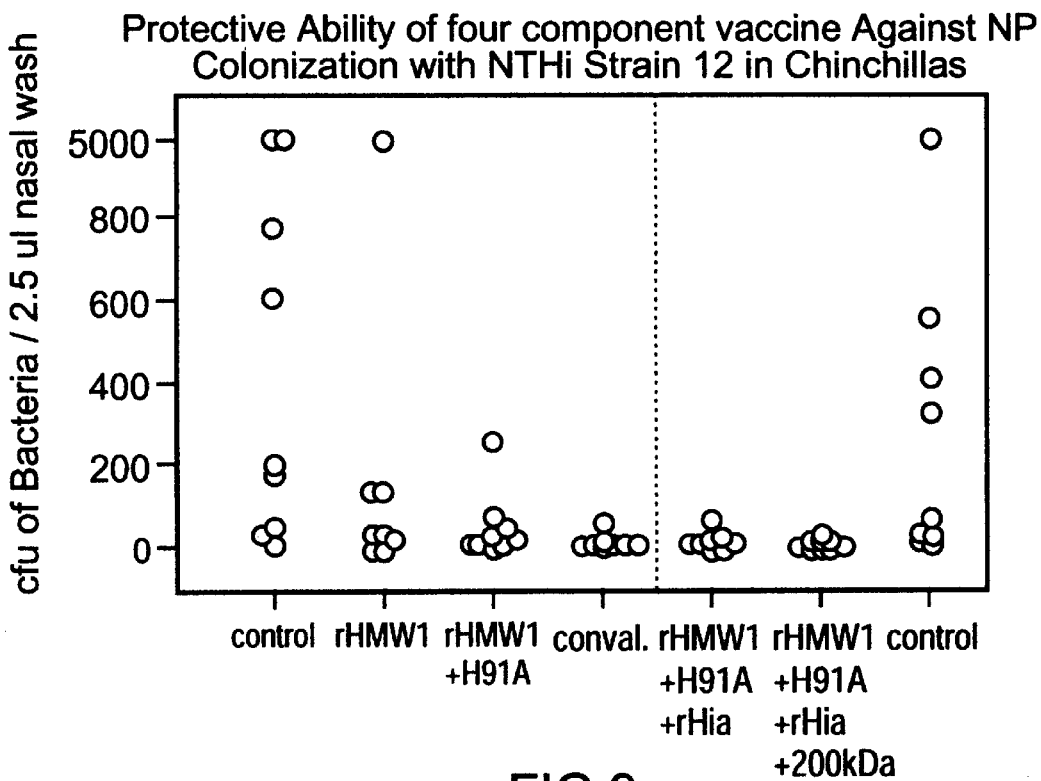
FIG. 9 shows the protection of the H91A Hin47+rHMW+ rHia+r200 kDa combination vaccine in the chinchilla model of nasopharyngeal colonization. The protection afforded by the four component vaccine is compared to that for a mono-component rHMW vaccine, a two component rHMW+H91A Hin47 vaccine, a three component rHMW+ H91A Hin47+rHia vaccine and convalescent controls.

Referring to FIG. 9, there is illustrated the protection afforded by the four component H91A Hin47+rHMW+ rHia+r200 kDa vaccine against nasopharyngeal colonization in a chinchilla model. The protection is comparable to that afforded by a mono-valent rHMW vaccine, a two component rHMW+H91A Hin47 vaccine and a three component rHMW+rHia+H91A Hin47 vaccine.

Figure 10:
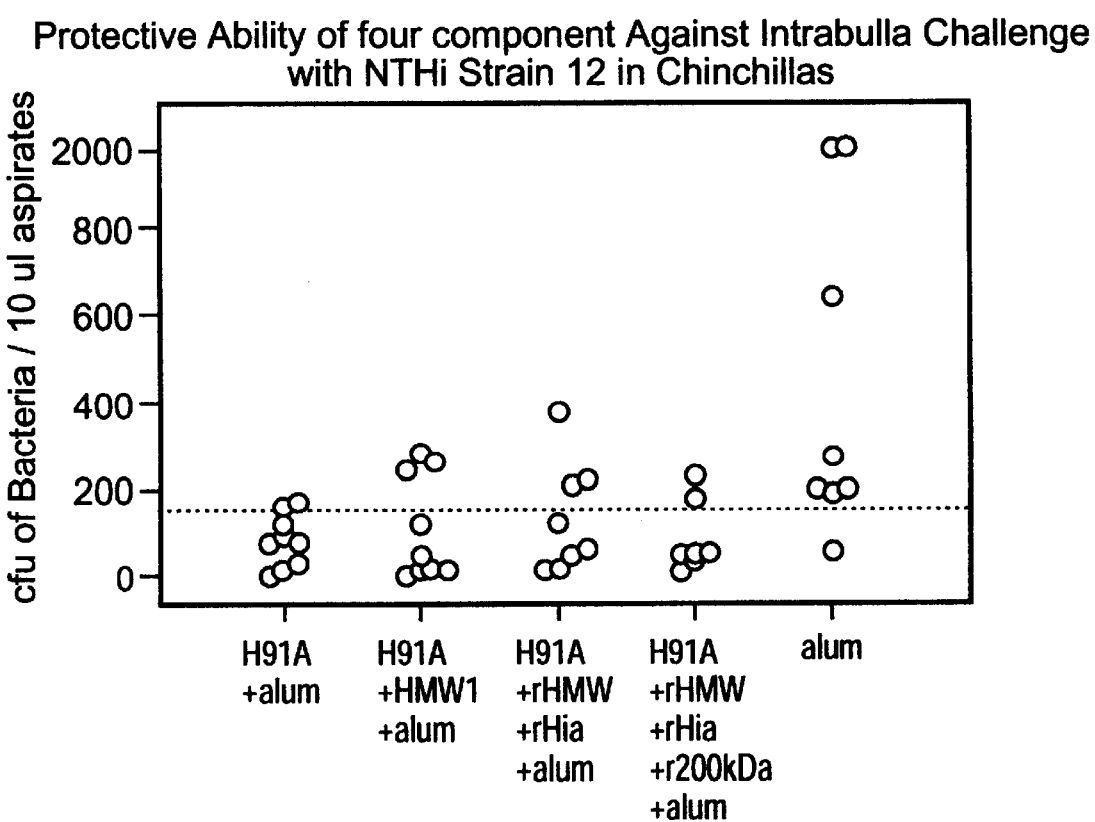
FIG. 10 illustrates the protection afforded by the H91A Hin47+rHMW+rHia+r200 kDa combination vaccine in the chinchilla model of intrabulla challenge. The protection afforded by the four component vaccine is compared to that for a mono-component H91A Hin47 (H91A) vaccine, a two component rHMW+H91A Hin47 vaccine, a three component rHMW+H91A Hin47+rHia vaccine and alum controls.

Referring to FIG. 10, there is illustrated the protection afforded by the four component H91A Hin47+rHMW+ rHia+r200 kDa vaccine against middle ear infection in a chinchilla model. The protection is comparable to that afforded by a mono-valent rHMW vaccine, a two component H91A Hin47+rHMW vaccine, and a three component H91A Hin47+rHMW+rHia vaccine.

EXAMPLES

The above disclosure generally describes the present invention. A more complete understanding can be obtained by reference to the following specific Examples. These Examples are described solely for purposes of illustration and are not intended to limit the scope of the invention. Changes in form and substitution of equivalents are contemplated as circumstances may suggest or render expedient. Although specific terms have been employed herein, such terms are intended in a descriptive sense and not for purposes of limitations.

Methods of molecular genetics, protein biochemistry, immunology and fermentation technology used, but not explicitly described in this disclosure and these Examples, are amply reported in the scientific literature and are well within the ability of those skilled in the art.

Example 1

This Example describes the preparation of the H91A Hin47 vaccine component.

The H91A Hin47 mutant was prepared as described in the aforementioned U.S. Pat. No. 5,506,139. Briefly, an oligonucleotide 5' ATCAATAACAGCATTATTGGT 3' (SEQ ID NO: 1) was synthesized which would change the Histidine residue at 91 to an Alanine (ref. 17).

Figure 11A:
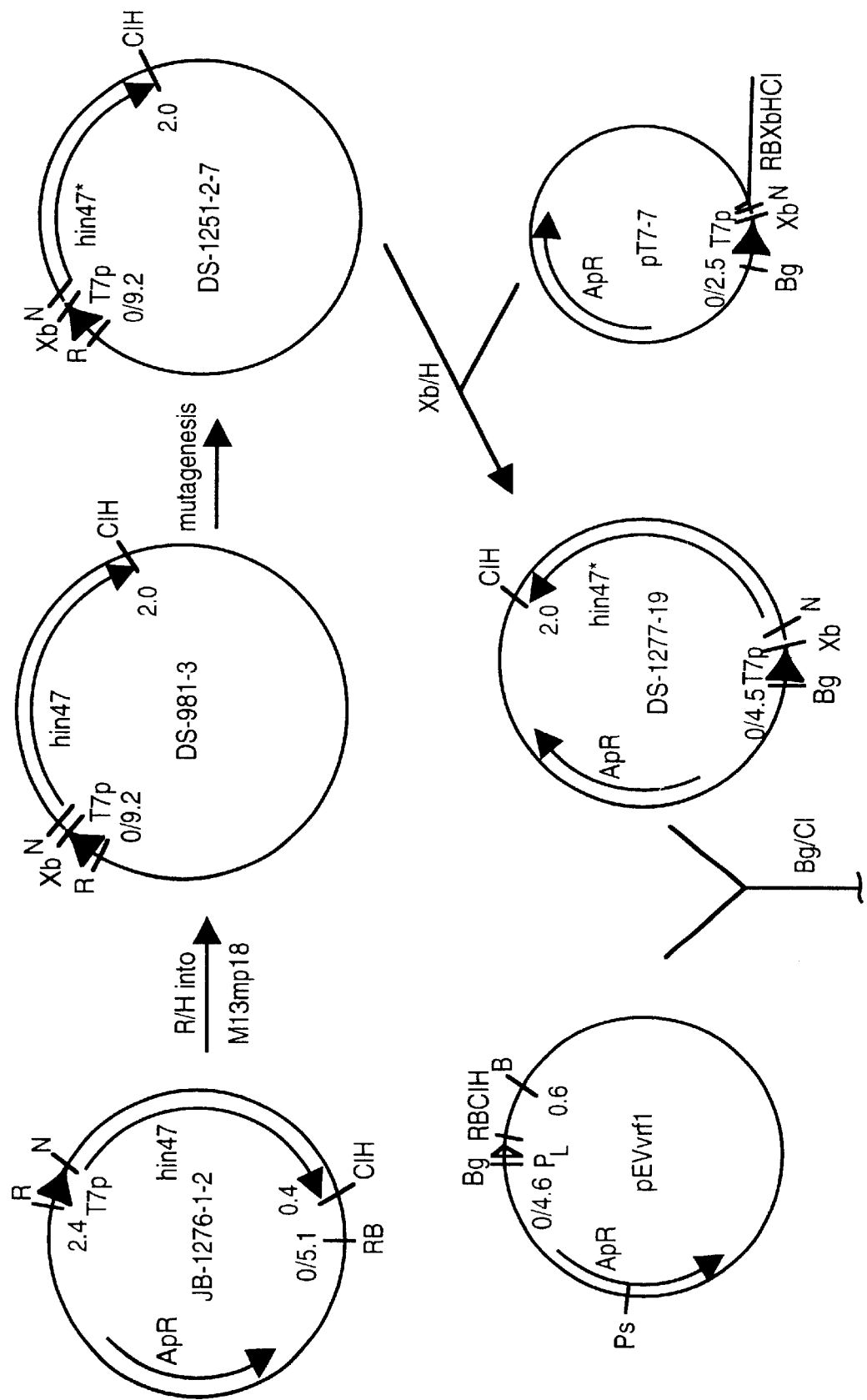
FIG. 11 is a schematic illustration of the construction scheme for producing plasmid DS-2150-1 containing the gene encoding the H91 Hin47 analog.
Figure 11B:
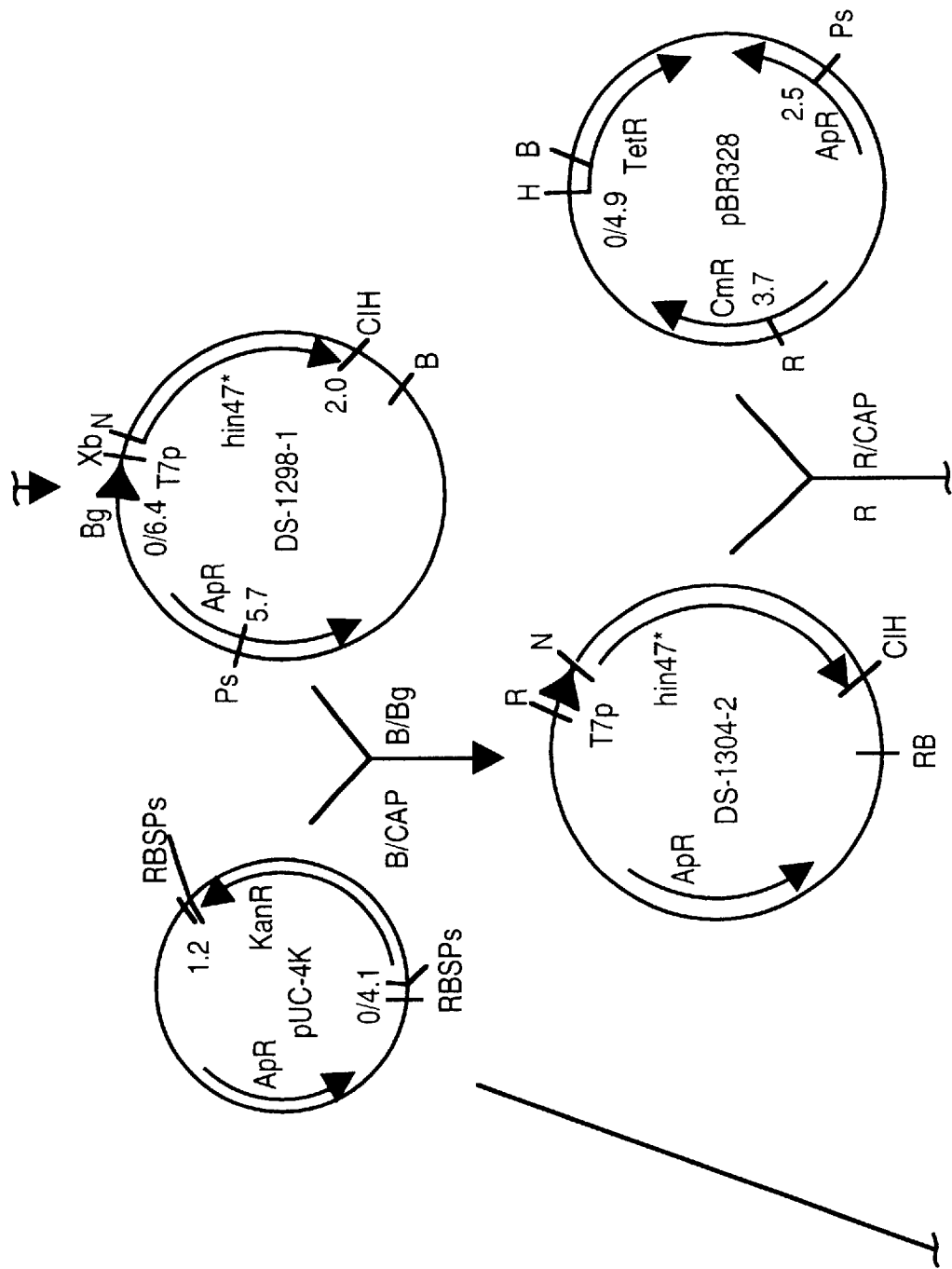
Figure 11C:
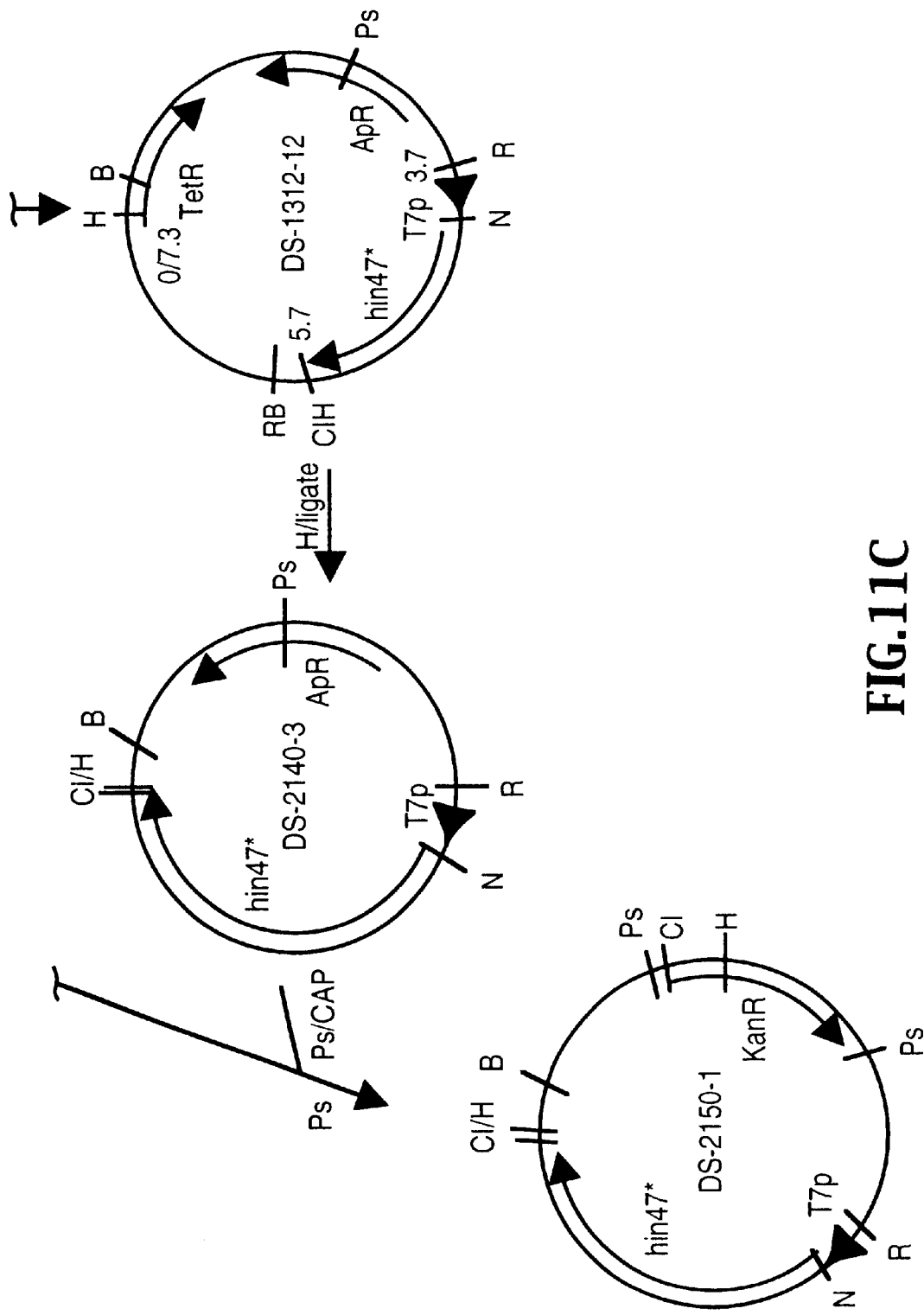

Plasmid JB-1276-1-2 is a pUC-based plasmid containing the T7/hin47 gene on an EcoR I fragment and was used to clone the hin47 gene into M13mp18 for site-directed mutagenesis with the In Vitro Site-Directed Mutagenesis kit from Amersham. The preparation of plasmid JB-1276-1-2 is described in U.S. Pat. No. 5,506,139. The mutation of the His91 codon to Ala91 was confirmed by local sequencing. The H91A mutant hin47 gene was subcloned into pT7-7 to generate plasmid DS-1277-19 (FIG. 11).

The H91A Hin47 expression plasmid (DS-1277-19) utilizes ampicillin selection. The T7/H91A hin47 gene was cloned into pBR328 so that tetracycline selection could be used. Vector DS-1312-12 was thus a pBR328-based plasmid which contained the T7/H91A hin47 gene sequences between EcoR I and Cla I sites, having functional ampicillin and tetracycline resistance genes and containing a repeat of the Hind III—BamH I sequences which are found in both pBR328 and pEVvrfl.

A new plasmid based upon DS-1312-12 was constructed which utilizes kanamycin selection. The construction scheme is shown in FIG. 11. Plasmid DNA from DS-1312-12 was digested with Hind III generating two fragments. The larger 5.9 kb fragment contained a promoterless tetR gene, the ampR gene and the T7/H91A hin47 gene and was re-ligated on itself creating vector DS-2140-3. Plasmid DS-2140-3 was digested with Pst I and the kanR gene from plasmid pUC-4K (P-L Biochemicals) was inserted into the Pst I site, generating plasmid DS-2150-1 which is kanR and sensitive to both ampicillin and tetracycline.

Plasmid DNA from DS-2150-1 was prepared from a 50 mL culture using a protocol based upon the Holmes and Quigley procedure (ref. 23) and including extractions with phenol and chloroform. E. coli BL21(DE3) cells were made electrocompetent as follows. Briefly, 10 mL of overnight culture were inoculated into 500 mL of YT medium and the cells were grown at 37° C. with shaking until they reached an $A_{620}$=0.540. The culture was chilled on ice for 30 min., spun at 5K rpm for 15 min., and the cell pellet resuspended in 500 mL ice cold sterile water. The cell suspension was centrifuged as before and the cell pellet resuspended in 250 mL ice cold sterile water. The cell suspension was spun again, and the cells were resuspended in 10 mL of 10% glycerol. The glycerol suspension was spun, and the cells were resuspended in 1.5 mL of 10% glycerol, aliquotted as 40 μl samples, and stored at −70° C.

One aliquot of electrocompetent BL21(DE3) cells was thawed on ice and approximately 9 ng of DS-2150-1 DNA was added. Samples were incubated on ice for 3 min. then transferred to a −20° C. BioRad Gene Pulser electrode cuvette and subjected to an electric pulse. 900 μl of SOC medium were added and the mixture transferred to a culture tube where it was incubated at 37° C. for 1 hour before being plated onto YT agar containing 25 μg/mL kanamycin. The plate was incubated overnight at 37° C. and single colonies were used for expression studies.

Individual clones were grown in NZCYM medium to an $A_{600\ nm}$ of approximately 0.3 and lactose was added to 1% to induce expression. Cells were grown for 4 hours, then harvested and analysed by SDS PAGE. Clone DS-2171-1-1 was chosen as a representative clone which expressed high levels of H91A Hin47.

The E. coli containing DS-2171-1-1 was grown in 2×2 L flasks containing 250 mL of ECGM (containing 8 g/L glucose, pH 6.5) and incubated by shaking at 37° C. for approximately 9 hours in the dark at 250 rpm. The culture fluid (2×250 mL) was inoculated into a 10 L fermentor and the culture grown at 37° C. After approximately 10 hours of incubation, 1% lactose (final concentration) is added for induction, followed by an additional 4 hours incubation.

The culture fluid was harvested into sterile transfer bottles and concentrated and diafiltered by cross-flow filtration against 50 mM Tris/HCl buffer, pH 8.0. The cells in the concentrate are lysed using a high-pressure homogenizer (2 passes at 15,000 psi) to release the H91A Hin47 protein. The cell debris was removed by centrifugation at 15,000 rpm for 1.5 hours. The supernatant was further clarified by centrifugation and filtered through a 0.22 μm dead-end filter. Products may be stored frozen at −70° C. until further processing.

Sodium chloride (NaCl) was added to the clarified sample to a final concentration of 100 mM. The sample was then purified on an anion exchange chromatography column (TMAE-Fractogel) equilibrated with 50 mM Tris pH 8.0 containing 100 mM NaCl. The H91A Hin47 protein was obtained in the run-through.

The aqueous layer was loaded onto a ceramic hydroxyapatite type 1 (CHTP-1) column equilibrated with 10 mM sodium phosphate buffer pH 8.0. The column was then washed with 150 mM sodium phosphate buffer pH 8.0 and H91A Hin47 was eluted with 175 mM sodium phosphate buffer, pH 8.0 containing 1 M NaCl.

The H91A Hin47 purified protein was concentrated using a 10 kDa molecular weight cut-off membrane followed by diafiltration with approximately 10 volumes of phosphate buffered saline (PBS), pH 7.5.

The H91A Hin47 purified protein in PBS was passed through a Q600 Sartobind membrane adsorber. After passing the solution, the membrane was regenerated using 1.0 M KCl/1.0 M NaOH followed by washing with 1 M KCl then equilibrating with PBS. The process was repeated twice. The concentrated diafiltered H91A Hin47 protein was sterile filtered through a 0.22 μm membrane filter. Sterile H91A Hin47 protein was adjuvanted with aluminum phosphate. The adsorbed purified concentrate was diluted to produce the adsorbed bulk at 400 μg/mL.

Example 2

This Example describes the preparation of the rHMW vaccine component.

The production and purification of the rHMW protein has been described in the aforementioned copending U.S. patent application Ser. No. 09/167,568 filed Oct. 7, 1998.

Figure 12:
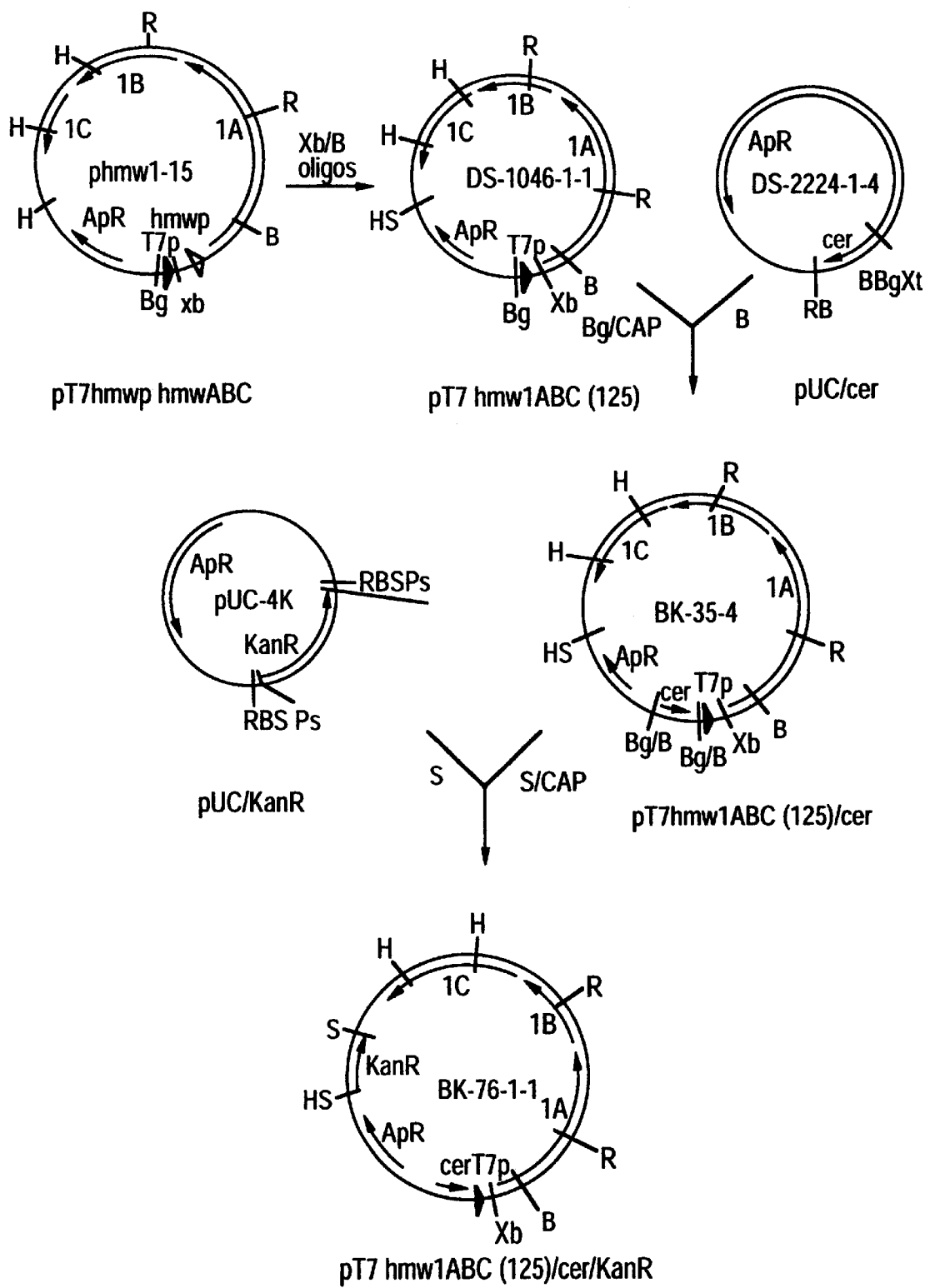
FIG. 12 is a schematic illustration of the construction scheme for producing plasmid BK-76-1-1 containing the hmw1ABC gene cluster from NTHi strain 12.

Briefly, plasmid pHMW1-15 (ref. 13) contains a Xba I site within the T7 promoter sequence and a unique BamH I site within the coding sequence of the mature HMW1A protein of non-typeable Haemophilus strain 12. The 1.8 kb Xba I-BamH I fragment of pHMW1-15 was deleted and replaced by an approximately 114 bp Xba I-BamH I fragment generated from oligonucleotides. The resultant 11.3 kb plasmid, DS-1046-1-1, thus contains the T7 promoter joined in frame with the hmw1ABC operon that encodes the mature 125 kDa HMW1A protein (FIG. 12).

Plasmid DS-1046-1-1 contains the T7 hmw1ABC gene cassette and has a unique Bgl II site outside the coding region of the mature HMW1A gene. Plasmid DS-2224-1-4 contains the *E. coli* cer gene located on a BamH I fragment. This fragment was isolated and ligated into the Bgl II site of plasmid DS-1046-1-1 to produce plasmid BK-35-4 (FIG. 12). The kanamycin resistance cassette was excised from pUC 4K by Sal I restriction and ligated into the Sal I restricted BK-35-4 plasmid to produce plasmid BK-76-1-1 (FIG. 12).

Plasmid DNA from BK-76-1-1 was prepared from a 50 mL culture using a protocol based upon the Holmes and Quigley procedure (ref. 23) and including extractions with phenol and chloroform. Plasmid DNA was introduced into *E. coli* BL21(DE3) cells by electroporation using a BioRad apparatus. Strains were grown at 37° C. in NZCYM medium to an optical density of $A_{578}=0.3$, then induced by the addition of lactose to 1.0% for 4 hours. Samples were adjusted to 0.2 OD/μl with SDS-PAGE lysis+loading buffer and the same amount of protein sample was loaded onto SDS-PAGE gels. Clone BK-116-1-1 was chosen as a representative clone that expressed good levels of rHMW.

Recombinant HMW protein was expressed as inclusion bodies in *E. coli*, and was purified as follows. *E. coli* cell pellets from 500 ml culture were resuspended in 50 ml of 50 mM Tris-HCl, pH 8.0, containing 0.1 M NaCl, and disrupted by sonication. The extract was centrifuged at 20,000 g for 30 min and the resultant supernatant was discarded. The pellet was further extracted, in 50 ml of 50 mM Tris-HCl, pH 8.0 containing 0.5% Triton X-100 and 10 mM EDTA, then centrifuged at 20,000 g for 30 min, and the supernatant was discarded. The pellet was further extracted in 50 ml of 50 mM Tris-HCl, pH 8.0, containing 1% octylglucoside, then centrifuged at 20,000 g for 30 min, and the supernatant was discarded.

The resultant pellet, obtained after the above extractions, contains the inclusion bodies. The pellet was solubilized in 6 ml of 50 mM Tris-HCl, pH 8.0, containing 6 M guanidine and 5 mM DTT. Twelve ml of 50 mM Tris-HCl, pH 8.0 was added to this solution and the mixture was centrifuged at 20,000 g for 30 min. The supernatant was precipitated with polyethylene glycol (PEG) 4000 at a final concentration of 7%. The resultant pellet was removed by centrifugation at 20,000 g for 30 min and the supernatant was precipitated by $(NH_4)_2SO_4$ at 50% saturation. After the addition of $(NH_4)_2SO_4$, the solution underwent phase separation with protein going to the upper phase, which was then subjected to centrifugation at 20,000 g for 30 min. The resultant pellet was dissolved in 2 ml of 50 mM Tris-HCl, pH 8.0, containing 6 M guanidine HCl and 5 mM DTT and the clear solution was purified on a Superdex 200 gel filtration column equilibrated in 50 mM Tris-HCl, pH 8.0, containing 2 M guanidine HCl . The fractions were analysed by SDS-PAGE and those containing the purified rHMW1 were pooled and dialysed overnight at 4° C. against PBS, then centrifuged at 20,000 g for 30 min. The protein remained soluble under these conditions and glycerol was added to the rHMW1 preparation at a final concentration of 20% for storage at −20° C.

The concentration of a rHMW vaccine component was adjusted to 400 μg $ml^{-1}$ in PBS (pH 7.3) and was adjuvanted with aluminum phosphate to a final concentration of 3 μg $ml^{-1}$. Different doses were prepared by diluting the stock with 3 μg $ml^{-1}$ aluminum phosphate in water.

Example 3

This Example illustrates the preparation of the rHia vaccine component.

The production and purification of the rHia protein has been described in the aforementioned copending U.S. patent application Ser. No. 09/268,347.

Figure 13:
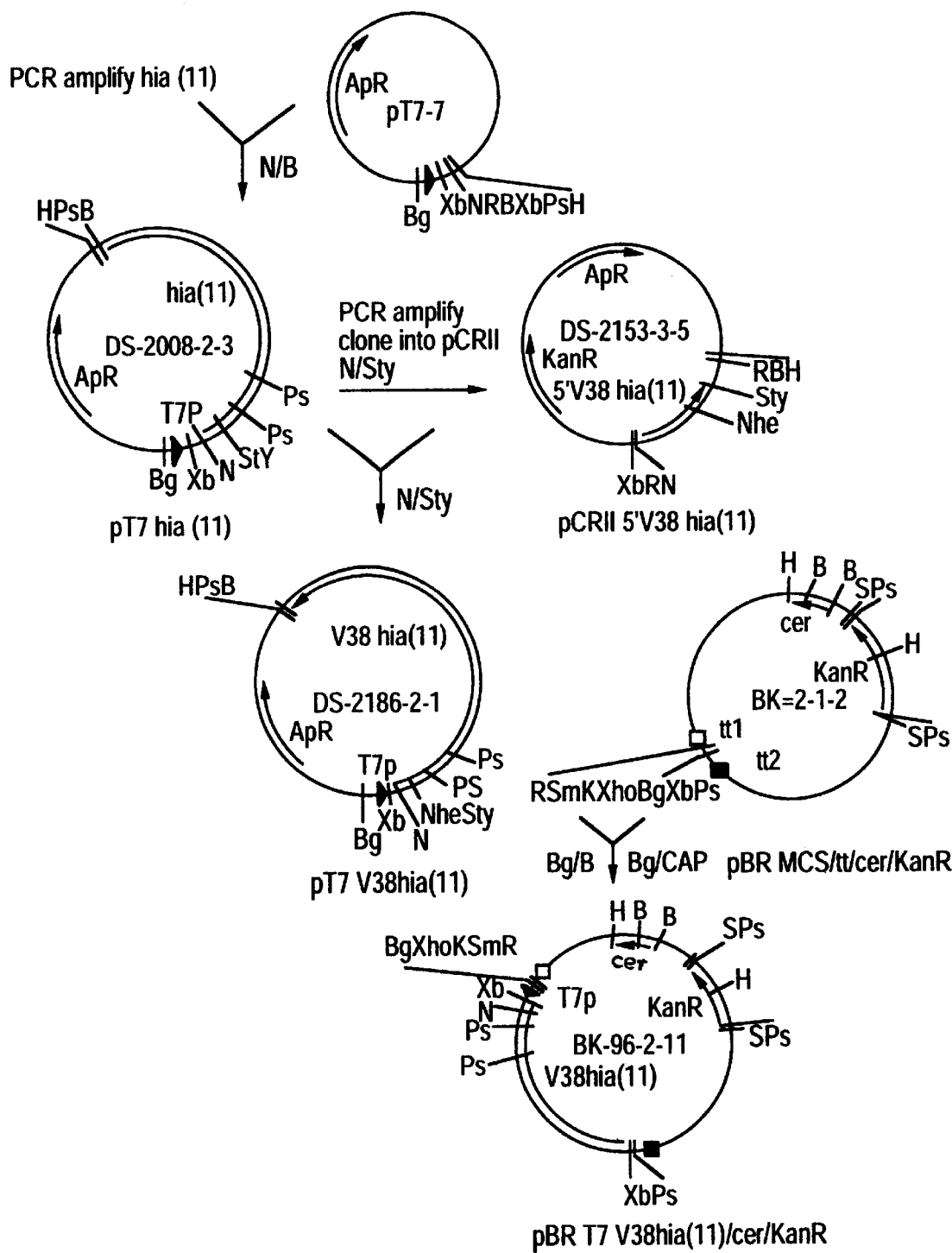
FIG. 13 is a schematic illustration of a construction scheme for producing plasmid BK-96-2-11 containing the gene encoding N-truncated V38 truncated Hia from NTHi strain 11.

Briefly, plasmid DS-1843-2 is a pBR328-based plasmid in which a multiple cloning site and two transcription terminators have been introduced on oligonucleotides, between the EcoR I and Pst I sites, thus destroying both the chloramphenicol and ampicillin resistance genes (FIG. 6B). The kanamycin resistance gene from pUC-4K was inserted at the Sal I site, to generate plasmids DS-2147-1 that is kanamycin resistant and tetracycline sensitive. Plasmid DS-2224-1-4 is a pUC plasmid containing a synthetic *E. coli* cer gene (ref. 15) constructed from oligonucleotides and flanked by BamH I sites. The 290 bp BamH I fragment of the cer gene was inserted into the BamH I site of DS-2147-1 creating plasmid BK-2-1-2. This pBR-based plasmid thus contains a multiple cloning site, the kanamycin resistance gene and the cer gene. Plasmid BK-2-1-2 was linearized with Bgl II and dephosphorylated. Plasmid DS-2186-2-1 was digested with Bgl II and BamH I and the 3.6 kb T7 V38 hia fragment was inserted into BK-2-1-2, creating plasmid BK-96-2-11 (FIG. 13).

Plasmid DNA from BK-96-2-11 was prepared from a 50 ml culture using a protocol based upon the Holmes and Quigley procedure (ref. 23) and including extractions with phenol and chloroform. Plasmid DNA was introduced into electrocompetent *E. coli* BL21 (DE3) cells by electroporator using a BioRad electroporator. Strains were grown at 37° C. in NZCYM medium using the appropriate antibiotic selection to an optical density of $A_{578}$ of 0.3 before induction by the addition of lactose to 1.0% for 4 hours. Samples were adjusted to 0.2 OD/µl with SDS-PAGE lysis+loading buffer and the same amount of each protein sample was loaded onto SDS-PAGE gels. Clone BK-131-1-1 was chosen as a representative clone that expressed good levels of V38 rHia (FIG. 13).

Recombinant truncated Hia protein was expressed as inclusion bodies in *E. coli* and was purified as follows. *E. coli* cell pellets from 500 ml culture were resuspended in 50 ml of 50 mM Tris-HCl, pH 8.0, containing 0.1 M NaCl, and disrupted by sonication. The extract was centrifuged at 20,000 g for 30 min and the resultant supernatant was discarded. The pellet was further extracted, in 50 ml of 50 mM Tris-HCl$_1$, pH 8.0 containing 0.5% Triton X-100 and 10 mM EDTA, then centrifuged at 20,000 g for 30 min, and the supernatant was discarded. The pellet was further extracted in 50 ml of 50 mM Tris-HCl, pH 8.0, containing 1% octylglucoside, then centrifuged at 20,000 g for 30 min, and the supernatant was discarded.

The resultant pellet obtained after the above extractions contains the inclusion bodies. The pellet was solubilized in 6 ml of 50 mM Tris-HCl, pH 8.0, containing 6 M guanidine and 5 mM DTT. Twelve ml of 50 mM Tris-HCl, pH 8.0 was added to this solution and the mixture was centrifuged at 20,000 g for 30 min. The supernatant was precipitated with polyethylene glycol (PEG) 4000 at a final concentration of 7%. The resultant pellet was removed by centrifugation at 20,000 g for 30 min and the supernatant was precipitated by $(NH_4)_2SO_4$ at 50% saturation. The $(NH_4)_2SO_4$ precipitate was collected by centrifugation at 20,000 g for 30 min. The resultant pellet was dissolved in 2 ml of 50 mM Tris-HCl, pH 8.0, containing 6 M guanidine HCl and 5 mM DTT and the clear solution was purified on a Superdex 200 gel filtration column equilibrated in 50 mM Tris-HCl, pH 8.0, containing 2 M guanidine HCl. The fractions were analysed by SDS-PAGE and those containing the purified rHia were pooled and dialysed overnight at 4° C. against PBS, then centrifuged at 20,000 g for 30 min. The protein remained soluble under these conditions and glycerol was added to the rHia preparation at a final concentration of 20% for storage at –20° C.

The concentration of the rHia vaccine component was adjusted to 400 µg ml$^{-1}$ in PBS (pH 7.3) and was adjuvanted with aluminum phosphate to a final concentration of 3 mg ml$^{-1}$. Different doses were prepared by diluting the stock with 3 mg ml$^{-1}$ aluminum phosphate in H$_2$O.

Example 4

This Example illustrates the preparation of the r200 kDa vaccine component.

The production and purification of the r200 kDa protein has been described in the aforementioned copending U.S. patent application Ser. No. 09/361,619 filed Jul. 27, 1999.

Figure 14A:
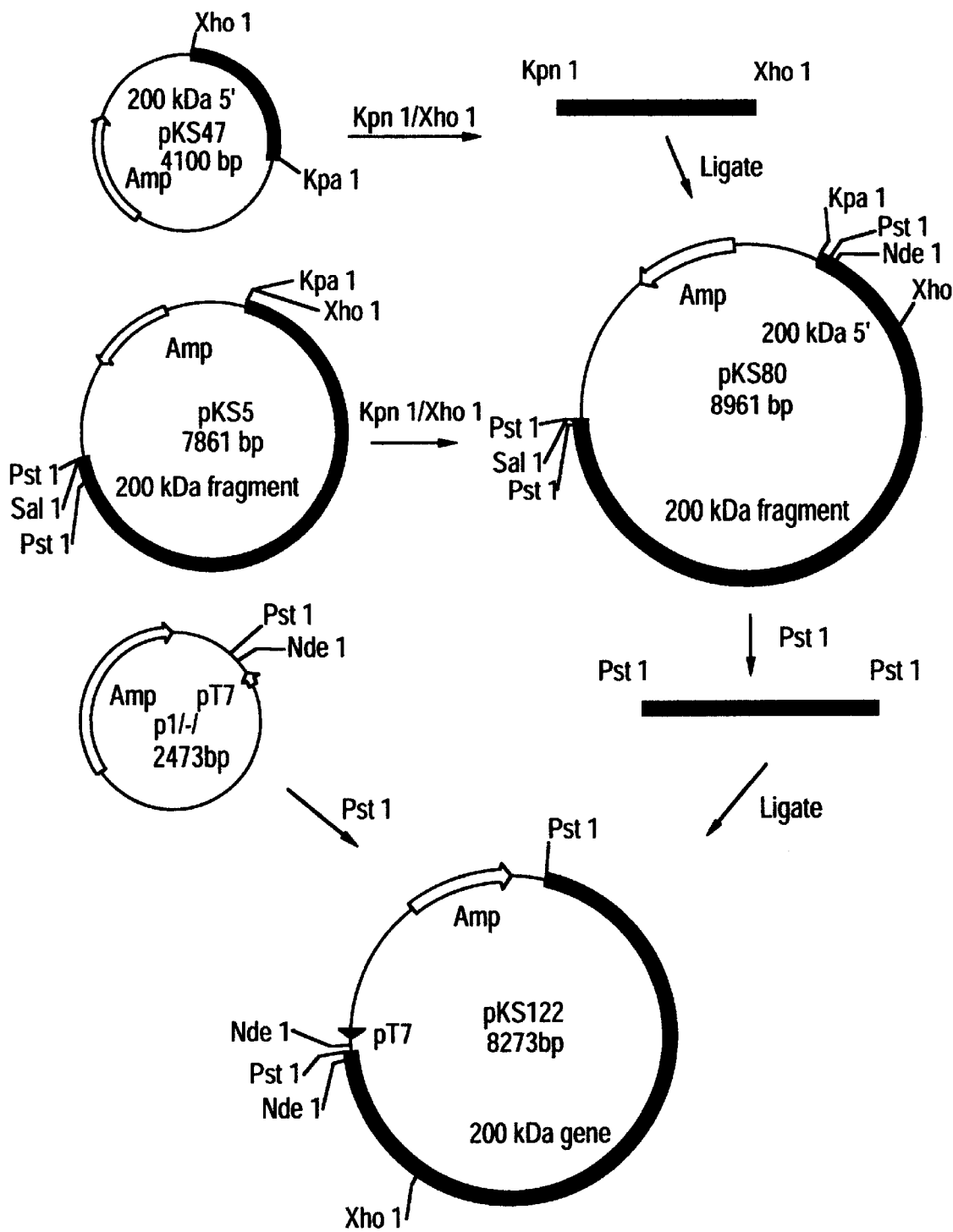
FIGS. 14A and 14B are a schematic illustration of a construction scheme for producing plasmid pKS348 containing the gene encoding N-truncated V56 r200 kDa from *M. catarrhalis* strain 4223.
Figure 14B:
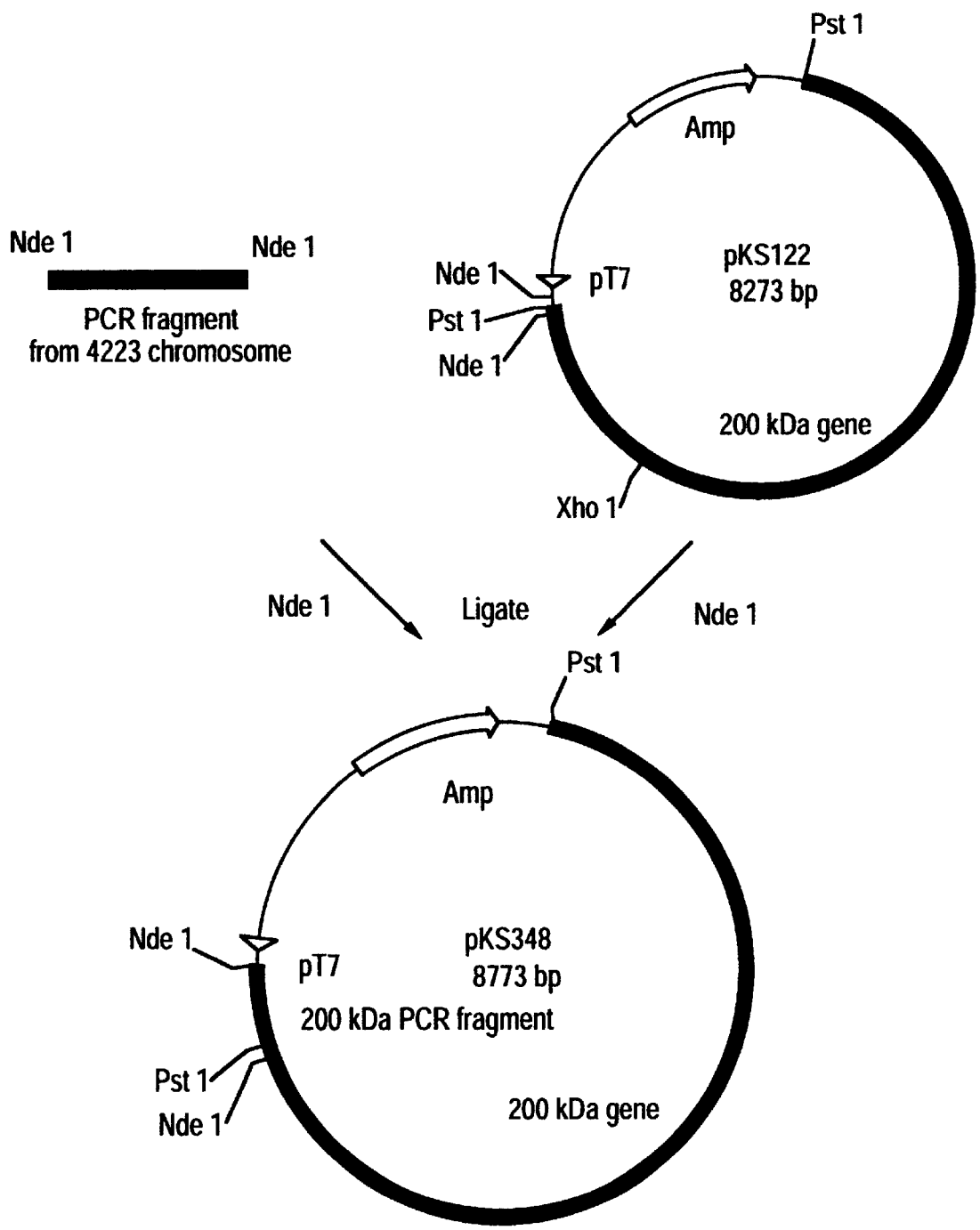

U.S. Pat. No. 5,808,024, assigned to the assignee hereof and the disclosure of which is incorporated herein by reference, and WO 96/34960 describe the isolation from genomic a *M. catarrhalis* genomic library in phrage lambda clone 8II which expressed the about 200 kDa protein. DNA was extracted and a series of plasmid vectors was prepared from DNA fragments. Plasmid pKS348 was constructed as shown schematically in FIGS. 14 and 14B. Plasmid pKS47, containing a 1—1 kb KpnI/XhoI fragment, was digested with XhoI and KpnI and separated by agarose gel electrophoresis. The 1.1 kb fragment was isolated from the gel and inserted into plasmid pKS5 containing a 4.9 kb XhoI/SalI fragment, which had previously been digested with the same two enzymes and purified to form pKS80. An about 5.8 kb PstI fragment from pKS80 was inserted into pT7-7 vector (ref. 24) that had been digested with PstI and dephosphorylated. The orientation of the insert was determined by restriction enzyme analysis and pKS122 was chosen for further construction (see FIG. 14A).

An about 500 bp 5' region of the 200 kDa gene was PCR amplified from *M. catarrhalis* strain 4223 from chromosomal DNA using primers 5471.KS (CGCTCGCTGTCCATATGATCGGTGAACGCTCA - SEQ ID No: 2) and 4257.KS (GACCCTGTGCATATGACATGGCT - SEQ ID No: 3), using the condition described in the aforementioned U.S. patent application Ser. No. 09/361,619. The PCR-product was digested with NdeI, purified and inserted into NdeI digested and dephosphorylated pKS122 to provide pKS348 (see FIG. 14B). Plasmid pKS348 was confirmed by restriction enzyme analyses and by sequencing of the PCR-amplified DNA piece and its joint regions. Such plasmid contains nucleic acid encoding an N-truncated about 200 kDa protein in which the codon encoding V56 amino acid is replaced by a start codon encoding M56 amino acid (M56 r200 kDa protein).

A single colony of *E. coli*, BL21(DE3)/pLysS, (KS358) which carried pKS348, was suspended in 5 ml of BHI broth containing Amp (100 µM) and 0.4% of glucose, and cultured overnight at 37° C. 2.5 ml of the overnight culture was added to 250 ml of LB (luria-Bertani) broth containing Amp (100 µM) and Cm (50 µM), and grown with shaking at 37° C. to $A_{600}$=0.26 to 0.44. Gene expression from the cultures was induced by addition of IPTG (final concentration: 4 mM). The bacteria were grown and harvested at different time points by centrifugation. The expression of the 200 kDa protein gene in the culture was confirmed by SDS-PAGE analysis using Coomassie Blue staining and by Western blot analysis using guinea pig anti-200 kDa protein serum, as described in U.S. Pat. No. 5,808,024 and WO 96/34960.

When *E. coli* BL21(DE3)/pLysS was transformed with pKS348, transformants grew well even on LB agar plates and in LB broth containing antibiotics at 37° C. After induction with IPTG, these clones produced a large amount of the N-terminally truncated r200 kDa protein. The N-terminally truncated r200 kDa protein was purified from the *E. coli* culture, as shown in FIG. 13.

*E. coli* cell pellets were obtained from the cultures prepared by centrifugation and were resuspended in 50 ml of 50 mM Tris-HCl, pH 8.0, containing 0.1 M NaCl, and disrupted by sonication. The sonicate was centrifuged at 20,000 xg for 30 min. and the resultant supernatant was discarded. The pellet was extracted, in 50 ml of 50 mM Tris-HCl, pH 8.0 containing 0.5% Triton X-100 and 10 mM EDTA, then centrifuged at 20,000×g for 30 min. and the supernatant was discarded. The pellet was further extracted in 50 ml of 50 mM Tris-HCl, pH 8.0, containing 1% octylglucoside, then centrifuged at 20,000×g for 30 min. and the supernatant was discarded.

The resultant pellet contained the inclusion bodies. The pellet was solubilized in 6 ml of 50 mM Tris-HCl, pH 8.0, containing 6 M guanidine and 5 mM DTT. Twelve ml of 50 mM Tris-HCl, pH 8.0 was added, the mixture centrifuged at 20,000×g for 30 min. and the pellet discarded. The supernatant was precipitated by adding polyethylene glycol (PEG) 4000 at a final concentration of 5% and incubated at 4° C. for 30 min. the resultant pellet was removed by centrifugation at 20,000 xg for 30 min. The supernatant was then precipitated by $(NH_4)_2SO_4$ at 50% saturation at 4° C. overnight. After the addition of $(NH_4)_2SO_4$, the solution underwent phase separation with protein going to the upper phase (as judged by the cloudiness of the layer). The upper phase was collected, then subjected to centrifugation at 20,000×g for 30 min. The resultant pellet was collected and dissolved in 2 ml of 50 mM Tris-HCl, pH 8.0, containing 6 M guanidine and 5 mM DTT. The clear solution was purified on a Superdex 200 gel filtration column equilibrated in 50 mM Tris-HCl, pH 8.0, containing 2 M guanidine HCl. The fractions were analysed by SDS-PAGE and those containing the purified r200 kDa were pooled. The pooled fraction was concentrated 5 to 10 fold using a centriprep 30 and then dialysed overnight at 4° C. against PBS, and centrifuged at 20,000×g for 30 min to clarify.

The protein remained soluble under these conditions and glycerol was added to the M56 r200 kDa preparation at a final concentration of 20% for storage at −20° C. The average yield of the purified M56 r200 kDa protein is about 10 mg $L^{-1}$ culture.

The concentration of the r200 kDa vaccine component was adjusted to 400 $\mu$g $ml^{-1}$ in PBS (pH 7.3) and was adjuvanted with aluminum phosphate to a final concentration of 3 mg $ml^{-1}$. Different doses were prepared by diluting the stock with 3 mg $ml^1$ aluminum phosphate in $H_2O$.

Example 5

This Example describes the combination of H91A Hin47+ rHMW+rHia+r200 kDa as a four component vaccine.

The preparation of a three component vaccine comprising H91A Hin47+rHMW+rHia has been described in the aforementioned copending U.S. patent application Ser. No. 09/261,182.

Briefly, vaccines were prepared -that comprised combination of rHia with a two-component H91A Hin47 and rHMW vaccine, prepared as described in copending U.S. patent application Ser. No. 09/210,995. The components were combined on day 0, mixed overnight at 4° C. and aliquotted on day 1. The combined vaccines were stored at 4° C. throughout the immunization period.

Vaccines were prepared that comprised the following combinations of r200 kDa with the three component vaccine as in Table II:

TABLE II

| μg r200 kDa→ / μg 3 Component↓ | 0 | 0.3 | 1.0 | 3.0 | 10.0 | 25 | 50 | 100 |
|---|---|---|---|---|---|---|---|---|
| 0 | | m | m | m | m | gp | gp | gp |
| 0.3 + 0.3 + 0.3 | m | m | m | m | m | | | |
| 3.0 + 3.0 + 3.0 | m | m | m | m | m | | | |
| 25 + 25 + 25 | gp | | | | | gp | gp | gp |
| 50 + 50 + 50 | gp | | | | | gp | gp | gp |

Notes:
3 component refers to H91A Hin47 + rHMW + rHia
m indicates the vaccine was used to immunize mice.
gp indicates that the vaccine was used to immunize guinea pigs.

Vaccine components in Table II were combined on day 0, mixed overnight at 4° C. and aliquotted on day 1. All vaccines were stored at 4° C. throughout the immunization period.

Example 6

This Example describes the analysis of the immunogenicity of the multi-component vaccines in animals.

The immunogenicity of a three-component vaccine comprising H91A Hin47+rHMW+rHia, has been described in the aforementioned copending U.S. patent application Ser. No. 09/261,182.

Groups of five BALB/c mice (Charles River, Quebec) were immunized subcutaneously (s.c.) on days 1, 29 and 43 with one of the mouse vaccines described in Example 5. Blood samples were taken on days 0, 14, 28, 42, and 56.

Groups of five Hartley outbred guinea pigs (Charles River, Quebec) were immunized intramuscularly (i.m.) on days 1, 29 and 43 with one of the guinea pig vaccines described in Example 5. Blood samples were taken on days 0, 14, 28, 42, and 56.

Anti-H91A Hin47, anti-rHMW, anti-rHia and anti-r200 kDa IgG antibody titers were determined by antigen specific enzyme linked immunosorbent assays (ELISAs). Microtiter wells (NuncMAXISORB, Nunc, Denmark) were coated with 100 $\mu$l of protein solution (0.2 $\mu$g $ml^{-1}$). The secondary antibodies used were affinity-purified $F(ab')_2$ fragments of goat anti-mouse IgG (Fc-specific) or anti-guinea pig IgG (Fc-specific) antibodies conjugated to horseradish peroxidase (Jackson ImmunoResearch Labs, Mississauga, Ontario). The reactions were developed using tetramethylbenzidine (TMB/H202, ADI, Mississauga, Ontario) and absorbancies were measured at 450 nm (using 540 nm as a reference wavelength) in a Flow Multiskan MCC microplate reader (ICN Biomedicals, Mississauga, Ontario). The reactive titer of an antiserum was defined as the reciprocal of the dilution consistently showing a two-fold increase in absorbance over that obtained with the pre-bleed serum sample.

The results of the immunogenicity studies are illustrated in FIGS. 1A to 8C. As shown in FIG. 1A and 1B, the final bleed sera obtained from mice immunized with 0.3 $\mu$g, or 3.0 $\mu$g each of H91A Hin47+rHMW+rHia with 0, 0.3, 1.0, 3.0 or 10.0 $\mu$g of added r200 kDa, all had high antibody titers to H91A Hin47 component. With the low dose three component vaccine, there may be a synergistic effect on the primary anti-H91A Hin47 response with added r200 kDa.

As shown in FIGS. 2A and 2B, the final bleed sera obtained from mice immunized with 3.0 $\mu$g each of H91A Hin47+rHMW+rHia with 0, 0.3, 1.0, 3.0 or 10.0 μg of added r200 kDa, all had high titer antibodies to the rHMW component. The low dose vaccine was poorly immunogenic. There was no apparent enhancing or inhibiting effect on the anti-rHMW response with the addition of the r200 kDa component.

As shown in FIGS. 3A and 3B, the final bleed sera obtained from mice immunized with 0.3 μg each of H91A Hin47+rHMW+rHia with 0, 0.3, 1.0, 3.0 or 10.0 μg of added r200 kDa, all had high titer antibodies to the rHia component. There was no apparent enhancing or inhibiting effect on the anti-rHia response with the addition of the r200 kDa component.

As shown in FIGS. 4A to 4D, the final bleed sera obtained from mice immunized with 10.0 μg of r200 kDa added to 0, 0.3 μg or 3.0 μg each of H91A Hin47+rHMW+rHia, all had high titer antibodies to the r200 kDa component. There was no apparent enhancing or inhibiting effect on the anti-r200 kDa response with the addition of the other vaccine components. However, at lower doses of r200 kDa, the vaccine was poorly immunogenic and at the 1.0 μg dose, there is a statistically significant inhibitory effect of the added components on the anti-r200 kDa response.

The data in mice demonstrate the preferred nature of the composition of a multi-component vaccine by preventing suppression of responses to individual antigens.

The immunogenicity in guinea pigs is illustrated in FIGS. 5A to 8C. As shown in FIGS. 5A and 5B, the final bleed sera obtained from guinea pigs immunized with 25 μg or 50 μg each of H91A Hin47+rHMW +rHia with 0, 25, 50 or 100 μg of added r200 kDa, all had high titer antibodies to the H91A Hin47 component. There was no apparent enhancing or inhibiting effect on the anti-H91A Hin47 response upon the addition of the r200 kDa antigen.

As shown in FIGS. 6A and 6B, the final bleed sera obtained from guinea pigs immunized with 25 μg or 50 μg each of H91A Hin47+rHMW+rHia with 0, 25, 50 or 100 μg of added r200 kDa, all had high titer antibodies to the rHMW component. There was no apparent enhancing or inhibiting effect on the anti-rHMW response upon the addition of the r200 kDa antigen.

As shown in FIGS. 7A and 7B, the final bleed sera obtained from guinea pigs immunized with 25 μg or 50 μg each of H91A Hin47+rHMW+rHia with 0, 25, 50 or 100 μg of added r200 kDa, all had high titer antibodies to the rHia component. There was no apparent enhancing or inhibiting effect on the anti-rHia response upon the addition of the r200 kDa antigen.

As shown in FIGS. 8A, 8B and 8C the final bleed sera obtained from guinea pigs immunized with 25, 50 or 100 μg of r200 kDa with added 0, 25 or 50 μg each of H91A Hin47+rHMW+rHia, all had high titer antibodies to the r200 kDa component. There was a statistically significant effect on the anti-r200 kDa antibody titers for some of the interim bleeds, when increasing amounts of the other components were added. However, there was no significant effect on the final bleeds.

Example 7

This Example describes the protective ability of a multi-component vaccine in animal models of disease.

In young chinchillas, it has been demonstrated that nasopharyngeal colonization with non-typeable *H. influenzae* leads to otitis media (ref. 17). rHMW is partially protective in a chinchilla nasopharyngeal colonization challenge model, as described in the aforementioned U.S. patent application Ser. No. 09/167,568. In this model, animals are immunized i.m. on days 0, 14 and 28 with 25, 50 or 100 μg of rHMW adsorbed to alum, and challenged on day 44 with $10^8$ cfu of live bacteria delivered intranasally (50 μl per nares). Nasopharyngeal lavage is performed 4 days post challenge using 1 ml of sterile saline as wash. 25 μl of wash is plated onto chocolate agar in the presence of streptomycin and the plates incubated at 37° C. for 24 h. (The challenge stain was made streptomycin resistant by serial passaging, in order to facilitate the quantitation of recovered bacteria in the presence of natural flora that are killed by the streptomycin.) Convalescent animals or those mock-immunized with alum alone, are used as controls. For the multi-component vaccine study, 50 μg of each of H91A Hin47, rHMW, rHia and r200 kDa was mixed as described in Example 5 and chinchillas were immunized as described above. The results of the protection study are shown in FIG. 9 which indicates that there is still excellent protection afforded in the nasopharyngeal colonization challenge model by the combination of rHMW+rHia+H91A Hin47+ r200 kDa.

H91A Hin47 is partially protective in the chinchilla model of otitis media, as described in the aforementioned U.S. Pat. No. 5,506,139. In this model, 1 to 2 year old chinchillas (Moulton Chinchilla Ranch, Rochester, Minn.) are immunized i.m. on days 0, 14 and 28 with 30 μg of H91A Hin47 adsorbed to alum, and challenged on day 44 with 50 to 350 cfu of live organisms delivered into the middle ear space via the epitympanic bulla (ref. 14). Animals are monitored by tympanometry and middle ear fluid is collected 4 days post challenge, mixed with 200 μl of BHI medium and dilutions plated onto chocolate agar plates that are incubated for 24 h at 37° C. Convalescent animals or those mock-immunized with alum alone, are used as controls. For the multi-component vaccine study, 50 μg of each of H91A Hin47, rHMW, rHia and r200 kDa were combined as described in Example 5 and chinchillas were immunized as described above. The results of the protection study are shown in FIG. 10 which indicates that there is still partial protection afforded in the intrabulla challenge model by the combination of rHMW+rHia+H91A Hin47+r200 kDa.

Example 8

This Example illustrates the bactericidal properties of the composition.

There is no relevant animal model for infection by *Moraxella catarrhalis* but a bactericidal antibody assay has been developed as a surrogate assay. Briefly, *M. catarrhalis* strain 4223 was cultured overnight in brain heat infusion (BHI) broth (Difco Laboratories, Detroit, Mich.) at 37° C. The overnight culture was subcultured into 10 ml BHI broth and grown to $A_{578}=0.5$.

Bacteria were diluted ($10^{-3}$ or $10^{-4}$) in Veronal buffered saline (VBS, pH 7.6) containing 140 mM NaCl, 93 mM $NaHCO_3$, 2 mM Na-barbiturate, 4 mM bartiuric acid, 0.5 mM $MgCl_2.6H_2O$, 0.4 mM $CaCl_2.2H_2O$, and 0.1% bovine serum albumin. Guinea pig anti-r200 kD serum and pre-immune control serum were heated at 56° C. for 30 min. to inactivate endogenous complement. Serum and antiserum were diluted in VBS, and placed on ice.

Twenty-five μl of diluted pre-immune serum or test antiserum were added to the wells of a 96-well Nunclon microtitre plate (Nunc, Roskilde, Denmark). Twenty-five μl of diluted bacterial cells were added to each of the wells. A guinea pig complement (Biowhittaker, Walkerville, Md.) was diluted 1:10 in VBS, and 25 μl portions were added to each well. The plates were incubated for 60 min., gently shaking at 70 rpm on a rotary platform. Fifty μl of each reaction mixture were plated onto Mueller Hinton agar plates (Becton-Dickinson, Cockeysville, Md.). The plates were incubated at 37° C. for 24 hours, and then left at room temperature for a further 24 hours. The number of colonies per plate was counted, and averaged values of colonies per plate were estimated from duplicate pairs.

When pre-immune serum plates were compared with PBS control plates (no serum), pre-immune serum had no bactericidal effect on the homologous strain 4223. Therefore, it was assumed that the number of colonies per plate on pre-immune serum plates represented 100% viability for each strain and percent bactericidal killing was calculated as follows:

$$100\% - \frac{\left[\begin{array}{c}\text{average number of colonies per plate} \\ \text{in anti-r200 kD antiserum group}\end{array}\right] \times 100}{\text{average number of colonies per plate in pre-immune serum group}}\%$$

Using this assay, the relative bactericidal antibody activity of anti-r200 kDa and anti-4 component (H91A Hin47+ rHMW+rHia+r200 kDa), antisera were compared and found to be equivalent. These data, set forth in Tables III and IV below, indicate that there is no adverse effect on the bactericidal activity of anti-r200 kDa antibody when antibodies to additional antigens are present.

SUMMARY OF THE DISCLOSURE

In summary of this disclosure, the present invention provides a multi-valent vaccine against disease caused by both *Haemophilus influenzae* and *Moraxella catarrhalis*, including otitis media, which has a wide spectrum of efficacy, and comprising three different antigens of *Haemophilus influenzae*, two of which different antigens is a adhesin, and an antigen of *Moraxella catarrhalis*, which is antigenically related to one of the antigens of *Haemophilus influenzae*. Modifications are possible within the scope of the invention.

TABLE III

PERCENT KILLING OF 4223 BY GP 1409-13 α r200kD (alum) AND GP 1449-53 rH91, α Hia, HMW, r200kD (alum)

| | ANTISERIUM DILUTION | | | | | | |
|---|---|---|---|---|---|---|---|
| | 1/32 | 1/64 | 1/128 | 1/256 | 1/512 | 1/1024 | 1/2048 |
| GP 1409-13 α r200kD (alum) | 83% | 57% | 32% | 25% | 20% | | |
| GP 1449-53 α rHia, rHMW, r200kD, rH91A (alum) | 71% | 47% | 15% | 17% | 5% | | |
| GP 1338-43 α r200kD | | | 100% | 99% | 99% | 96% | 78% |

LM613, 11.12.98

Based on $\log_{10}=-4$ dilution of 4223

Ave prebleed colony count was 482

TABLE IV

PERCENT KILLING OF 4223 BY COMBINATION ANTISERA

| | Bact. Dil = $\log_{10}$ −4 | | | | Bact. Dil = $\log_{10}$ −3 | | | |
|---|---|---|---|---|---|---|---|---|
| Antiserum dilution: | 1/64 | 1/256 | 1/1024 | 1/4096 | 1/64 | 1/256 | 1/1024 | 1/4096 |
| GP 1631-36 α rHia rH91A, rHMW, r200kD (FCA/FIA) | 72% | 41% | 49% | 43% | 12% | 0% | 30% | 9% |
| GP 1637 −40 α r200kD (FCA/FIA) | 90% | 76% | 59% | 38% | 88% | 715 | 26% | 3% |
| GP 1651-55 α rHia rH91A, rHMW, r200kD (alum) | 79% | 37% | 66% | 43% | 65% | 0% | 5% | 0% |
| GP 1656-60 α r200kD (alum) | 86% | 79% | 74% | 54% | 77% | 25% | 22% | 4% |
| GP 1338-43 α r200kD (control) | 975 | 95% | 84% | 59% | 92% | 89% | 77% | 47% |

LM615, 16.12.98

Ave. prebleed colony count at $\log_{10}$-4 dilution of 4223 was 720

Ave. prebleed colony count at $\log_{10}$-3 dilution of 4223 was 58

REFERENCES

1. Barbour, M. L., R. T. Mayon-White, C. Cole, D. W. M. Crook, and E. R. Moxon. 1995. The impact of conjugate vaccine on carriage of *Haemophilus influenzae* type b. J. Infect. Dis. 171:93–98.
2. Berkowitz et al. 1987. J. Pediatr. 110:509.
3. Claesson et al. 1989. J. Pediatr. 114:97.
4. Black, S. B., H. R. Shinefield, B. Fireman, R. Iliatt, M. Polen, E. Vittinghoff, The Northern California Kaiser Permanent Vaccine Study Center Pediatrics Group. Efficacy in infancy of oligosaccharide conjugal,) *Haemophilus influenzae* type b (HBOC) vaccine in a United States population of 61,080 children. 1991. Pediatr. Infect. Dis. J. 10:97–104.
5. Nitta, D. M., M. A. Jackson, V. F. Burry, and L. C. Olson. 1995. Invasive *Haemophilus influenzae* type f disease. Pediatr. Infect. Dis J. 14:157–160.
6. Waggoner-Fountain, L. A., J. O. Hendley, E. J. Cody, V. A. Perriello, and L. G. Donowitz. 1995. The emergence of *Haemophilus influenzae* types e and t as significant pathogens. Clin. Infect. Dis. 21:1 122–1324.
7. Madore, D. V. 1996. Impact of immunization on *Haemophilus influenzae* type b disease. Infectious Agents and Disease 5:8–20.
8. Bluestone, C. D. 1982. Current concepts in otolaryngology. Otitis media in children: to treat or not to treat? N. Engi. J. Med. 306:1399–1404.
9. Ioannidis, J. P. A., M. Worthington, J. K. Griffiths, and D. R. Snydman. 1995 Spectrum and significance of bacteremia due to *Moraxella catarrhalis*. Clin. Infect. Dis. 21:390–397.
10. Meyer, G. A., t. R. Shope, N. J. Waeker, Jr., and F. H. Lanningham. 1995 *Moraxella (Branhamella) catarrhalis* bacteremia in children. Clin. Pediatr. 34:146–150.
11. Enright, M. C. and M. H. McKenzie. 1997. *Moraxella (Branhamella) catarrhalis*- clinical and molecular aspects of a rediscovered pathogen. J. Med. Microbiol. 46:360–371.
12. Barenkamp, S. J., and F. F. Bodor. 1990. Development of serum bactericida activity following non-typable *Haemophilus influenzae* acute otitis media. Pediatr. Infect. Dis. 9:333–339.
13. Barenkamp, S. J., and J. W. St. Geme III. 1994. Genes encoding high-molecular weight adhesion proteins of non-typeable *Haemophilus influenzae* are part of gene clusters. Infect. Immun. 62:3320–3328.
14. St. Geme III J. W., V. V. Kumar, D. Cutter, and S. J. Barenkamp. 1998. Prevalence and distribution of the hmw and hia genes and the HMW and Hia adhesins among genetically diverse strains of non-typeable *Haemophilus influenzae*. Infect. Immun. 66:364–368
15. St. Geme III, J. W., S. Falkow, and S. J. Barenkamp. 1993. High-molecular-weight proteins of non-typeable *Haemophilus influenzae* mediate attachment to human epithelial cells. Proc. Natl. Acad. Sci. USA 90 :2875–2879.
16. Barenkamp, S. J. 1996. Immunization with high-molecular-weight adhesion proteins of non-typeable *Haemophilus influenzae* modifies experimental otitis media in chinchillas. Infect. Immun. 64:1246–1251.
17. Yang, Y. P., S. M. Loosmore, B. Underdown, and M. H. Klein. 1998. Nasopharyngeal colonization with non-typeable *H. influenzae*, in chinchillas. Infect. Immun. 66:1973–1980.
18. St. Geme, J. W. and D. Cutter. 1995. Evidence that surface fibrils expressed by *Haemophilus influenzae* type b promote attachment to human epithelial cells. Molec. Microbiol. 15:77–85.
19. Barenkamp, S. J. and J. W. St. Geme. 1996. Identification of a second family of high-molecular-weight adhesion proteins expressed by non-typeable *Haemophilus influenzae*. Molec. Microbiol. 19:1215–1223.
20. St. Geme, J. W., D. Cutter and S. J. Barenkamp. 1996. Characterization of the genetic locus encoding *Haemophilus influenzae* type be surface fibril. J. Bact. 178:6281–6287.
21. Retzlaff, C., Y. Yamamoto, P. S. Hoffman, H Friedman, and T. W. Klein. 1994. Bacterial heat shock proteins directly induce cytokine MRNA and interleukin-1 secretion in macrophage cultures. Infect. Immun. 62:5689–5693.
22. Loosmore, S. M., Y-P. Yang, R. Oomen, J. M. Shortreed, D. C. Coleman, and M. H. Klein. 1998. The *Haemophilus influenzae* HtrA protein is a protective antigen. Infect. Immun. 66:899–906.
23. Holmes, D. S. and Quigley, M. 1981. A rapid boiling method for the preparation of bacterial plasmids. Anal. Biochem. 114:193–197.
24. Tabor S. and Richardson C. C., 1985. A. bacteriophage T7 RNA polymerase/promoter system for controlled exclusive expression of specific genes. Proc. Natl. Acad. Sci. 82(4): 1074–1078.

What we claim is:

1. A multi-valent immunogenic composition for conferring protection in a host against disease caused by both *Haemophilus influenzae* and *Moraxella catarrhalis*, which comprises:
    (a) an isolated and purified analog of *Haemophilus influenzae* Hin47 protein having a decreased protease activity which is less than about 10% of natural Hin47 protein,
    (b) an isolated and purified *Haemophilus influenzae* adhesin (Hia) protein of a non-typeable strain of *Haemophilus influenzae*,
    (c) an isolated and purified high molecular weight (HMW) protein of a non-typeable strain of *Haemophilus influenzae*, and
    (d) an isolated and purified outer membrane protein of *Moraxella catarrhalis* having an apparent molecular mass of about 200 kDa, as determined by SDS-PAGE.

2. The composition of claim 1 wherein said Hin47, Hia, HMW and 200 kDa proteins are present in amounts which do not impair the individual immunogenicities of the proteins.

3. The composition of claim 2 wherein said analog of Hin47 protein is one in which at least one amino acid of the natural Hin47 protein contributing to protease activity has been deleted or replaced by a different amino acid and which has substantially the same immunogenic properties as natural Hin47 protein.

4. The composition of claim 3 wherein said at least one amino acid is selected from the group consisting of amino acids 91, 121 and 195 to 201 of natural Hin47 protein.

5. The composition of claim 4 wherein Serine-197 is replaced by alanine.

6. The composition of claim 4 wherein Histidine-91 is replaced by alanine, lysine or arginine.

7. The composition of claim 6 wherein Histidine-91 is replaced alanine.

8. The composition of claim 4 wherein Asp-121 is replaced by alanine.

9. The composition of claim 2 wherein said Hia protein is produced recombinantly.

10. The composition of claim 9 wherein said recombinantly-produced Hia protein is an N-terminal truncation to position 37 and having a valine at position 38 (V38 rHia).

11. The composition of claim 2 wherein said HMW protein is an HMW1 or HMW2 protein of a non-typeable strain of *Haemophilus influenzae*.

12. The composition of claim 11 wherein the HMW1 and HMW2 proteins are produced recombinantly.

13. The composition of claim 12 wherein said HMW1 and HMW2 proteins are isolated from the respective strain of non-typeable *Haemophilus influenzae* and possess respective molecular weights as set forth in the following Table:

| Molecular Weight | | non-typeable *H. influenzae* Strain | | | | |
| --- | --- | --- | --- | --- | --- | --- |
| (kDa) | 12 | JoyC | K21 | LCDC2 | PMH1 | 15 |
| Mature HMW1 | 125 | 125.9 | 104.4 | 114.0 | 102.4 | 103.5 |
| Protein: HMW2 | 120 | 100.9 | | 111.7 | 103.9 | 121.9. |

14. The composition of claim 2 wherein said 200 kDa protein is produced recombinantly.

15. The composition of claim 14 wherein recombinantly-produced 200 kDa protein is an N-terminal truncation V56 r200 kDa.

16. The composition of claim 1 further comprising an adjuvant.

17. The composition of claim 16 wherein said adjuvant is aluminum hydroxide or aluminum phosphate.

18. The composition of claim 1 comprising
    (a) about 25 to about 100 μg of the Hin47 protein analog, and
    (b) about 25 to about 100 μg of the Hia protein,
    (c) about 25 to about 100 μg of the HMW protein, and
    (d) about 25 to about 100 μg of the 200 kDa protein.

19. The composition of claim 1 further comprising at least one additional antigenic component for conferring protection against infection caused by another pathogen.

20. The composition of claim 1 wherein said at least one additional antigenic component is selected from the group consisting of diphtheria toxoid, tetanus toxoid, pertussis antigens, non-virulent poliovirus and PRP-T.

21. The composition of claim 20 wherein said pertussis antigens are selected from the group consisting of pertussis toxoid, filamentous hemagglutinin, pertactin and agglutinogens.

22. A method of immunizing a host against disease caused by infection with both *Haemophilus influenzae* and *Moraxella catarrhalis*, including otitis media, which comprises administering to the host an immunoeffective amount of a composition as claimed in claim 1.

* * * * *

SEQUENCE LISTING

<160> NUMBER OF SEQ ID NOS: 3

<210> SEQ ID NO 1
<211> LENGTH: 21
<212> TYPE: DNA
<213> ORGANISM: Haemophilus influenzae

<400> SEQUENCE: 1
atcaataaca gcattattgg t                                         21

<210> SEQ ID NO 2
<211> LENGTH: 33

-continued

```
<212> TYPE: DNA
<213> ORGANISM: Moraxella catarrhalis

<400> SEQUENCE: 2
cgctcgctgt ccatatgatc ggtgcaacgc tca                              33

<210> SEQ ID NO 3
<211> LENGTH: 23
<212> TYPE: DNA
<213> ORGANISM: Moraxella catarrhalis

<400> SEQUENCE: 3
gaccctgtgc atatgacatg gct                                        23
```